US007123953B2

(12) United States Patent
Starobin et al.

(10) Patent No.: US 7,123,953 B2
(45) Date of Patent: Oct. 17, 2006

(54) METHOD AND SYSTEM FOR EVALUATING ARRHYTHMIA RISK WITH QT-RR INTERVAL DATA SETS

(75) Inventors: Joseph M. Starobin, Greensboro, NC (US); Yuri B. Chernyak, Waltham, MA (US)

(73) Assignee: Mediwave Star Technology Inc., Greensboro, NC (US)

(*) Notice: Subject to any disclaimer, the term of this patent is extended or adjusted under 35 U.S.C. 154(b) by 427 days.

(21) Appl. No.: 10/308,821

(22) Filed: Dec. 3, 2002

(65) Prior Publication Data

US 2003/0130586 A1 Jul. 10, 2003

Related U.S. Application Data

(60) Provisional application No. 60/344,654, filed on Dec. 26, 2001.

(51) Int. Cl.
*A61B 5/04* (2006.01)
(52) U.S. Cl. ............... 600/516; 600/515; 600/517; 600/519; 600/521
(58) Field of Classification Search ........ 600/515–517, 600/519, 521
See application file for complete search history.

(56) References Cited

U.S. PATENT DOCUMENTS

| 4,870,974 A | 10/1989 | Wang .................... 128/700 |
| 5,020,540 A | 6/1991 | Chamoun ................ 128/703 |
| 5,117,834 A | 6/1992 | Kroll et al. .............. 128/705 |
| 5,148,812 A | 9/1992 | Verrier et al. ........... 128/704 |
| 5,323,783 A | 6/1994 | Henkin et al. ........... 128/703 |
| 5,419,338 A | 5/1995 | Sarma et al. ........... 128/703 |
| 5,560,370 A | 10/1996 | Verrier et al. ........... 128/705 |
| 5,713,367 A | 2/1998 | Arnold et al. ........... 128/704 |
| 5,792,065 A | 8/1998 | Xue et al. ................ 600/516 |
| 5,794,623 A | 8/1998 | Forbes .................... 128/702 |
| 5,827,195 A | 10/1998 | Lander .................... 600/509 |
| 5,842,997 A | 12/1998 | Verrier et al. ........... 600/518 |
| 5,891,047 A | 4/1999 | Lander et al. ........... 600/516 |
| 5,921,940 A | 7/1999 | Verrier et al. ........... 600/518 |
| 5,951,484 A | 9/1999 | Hoium et al. ........... 600/515 |

(Continued)

OTHER PUBLICATIONS

Arnold et al.; *The dependence on heart rate of the human ventricular action potential duration,* Cardiovascular Research, 16, 547-551 (1982).

(Continued)

*Primary Examiner*—Robert E. Pezzuto
*Assistant Examiner*—Tammie K. Heller
(74) *Attorney, Agent, or Firm*—Myers Bigel Sibley & Sajovec, PA

(57) ABSTRACT

A method of assessing the cardiac arrhythmia risk in a subject to provide a measure of cardiac or cardiovascular health in that subject is described herein. In one embodiment, the method comprises the steps of: (a) collecting at least one QT and RR interval data set from the subject; (b) separating fluctuations from slow trends in said at least one QT and RR interval data set; (c) comparing said QT and RR fluctuations to one another and (d) generating from the comparison of step (c) partial measures of risk of cardiac arrhythmia in said subject. A greater difference between QT and RR fluctuations indicates greater risk of cardiac arrhythmia in said subject. The data sets are collected in such a manner that they reflect almost exclusively the conduction in the heart muscle and minimize the effect on the data sets of rapid transients due to autonomic nervous system and hormonal control.

17 Claims, 15 Drawing Sheets

U.S. PATENT DOCUMENTS 6,361,503 B1 * 3/2002 Starobin et al. ............ 600/508

OTHER PUBLICATIONS

Chernyak et al.; *Class of Exactly Solvable Models of Excitable Media*, Phys. Rev. Lett,. 80:25, 5675-5678 (1998).

Chernyak et al.; *Where do dispersion curves end? A basic question in theory of excitable media*, Phys. Rev. E,. 58:4, 4108-4111 (1998).

Ciavolella et al.; *Exponential Fit of QT Interval-Heart Rate Relation During Exercise Used to Diagnose Stress-induced Myocardinal Ischemia*, Journal of Electrocardiology, 24:2, 145-153 (1991).

Cole et al.; *Heart-Rate Recovery Immediately After Exercise As A Predictor Of Mortality*, The New England Journal of Medicine, 341:18, 1351-1357 (Oct. 1999).

Franz et al.; *Cycle Length Dependence of Human Action Potential Duration In Vivo: Effects of Single Extrastimuli, Sudden Sustained Rate Acceleration and Deceleration, and Different Steady-State Frequencies*, J. Clin. Invest,. 82, 972-979 (1988).

Froelicher, Jr. et al.; *A comparison of three maximal treadmill exercise protocols*, Journal of Applied Physiology, 36:6, 720-725 (1974).

Hintze et al.; *Prognostic Properties of QT/RR Dynamics in Survivors of Myocardial Infarction with Reduced Systolic Function*, NASPE Annual Meeting, Washington, D.C. (May 17-20, 2000).

Jonnalegedda et al.; *An Exponential Formula for Heart Rate Dependence of QT Interval During Exercise and Cardiac Pacing in Humans: Reevaluation of Bazett's Formula*, Am J Cardiol, 54, 103-108 (1984).

Jonnalegedda et al.; *Hysteresis in the Human RR-QT Relationship During Exercise and Recovery*, PACE 10, 485-491 (1997).

Krahn, M.D. et al.; *Hysteresis of the RT Interval With Exercise; A New Marker for the Long-QT Syndrome?*, Circulation, 96, 1551-1556 (1997).

Lau et al.; *Hysteresis of the ventricular paced QT interval in response to abrupt changes in pacing rate*, Cardiovascular Research, 22, 67-72 (1988).

Starobin et al.; *The role of a critical excitation length scale in dynamics of reentrant cardiac arrhythmias*, Herzschr Elektrophys, 10, 119-136 (Month Unknown, 1999).

Surawicz; *Will QT Dispersion Play a Role in Clinical Decision-Making?*, J Cardiovascular Electrophysiol, 7, 777-784 (1996).

Swan et al.; *Rate adaption of QT intervals during and after exercise in children with congenital long QT syndrome*, European Heart Journal, 19, 508-513 (1998).

Takahashi et al.; *Paradoxically Shortened QT Interval after a Prolonged Pause*, PACE, 21, 1476-1479 (1998).

Pierpoint et al.; *Heart rate recovery post-exercise as an index of parasympathetic activity*, Journal of the Autonomic Nervous System, 80, 169-174 (May 12, 2000).

* cited by examiner

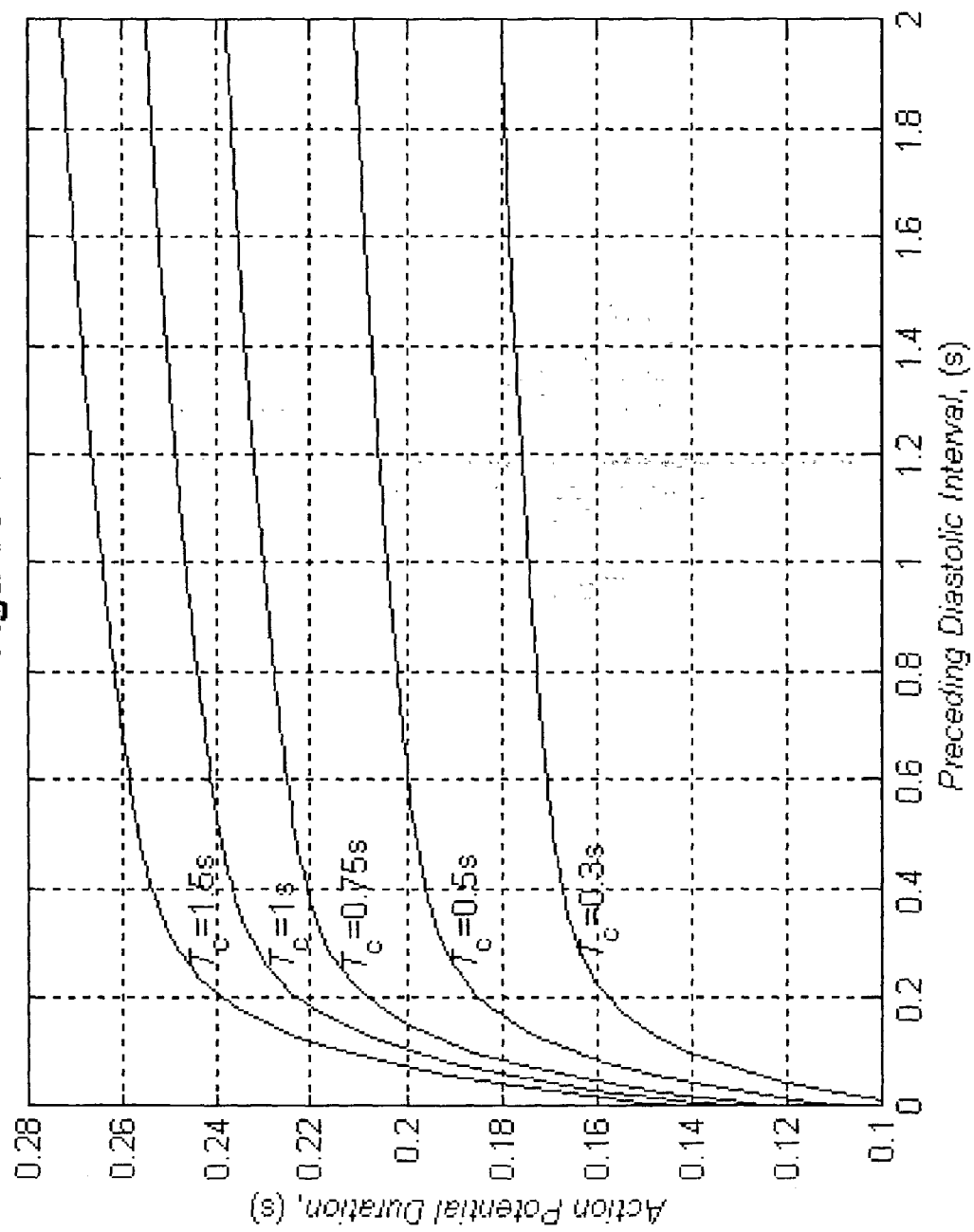

METHOD AND SYSTEM FOR EVALUATING ARRHYTHMIA RISK WITH QT-RR INTERVAL DATA SETS

RELATED APPLICATIONS

This application claims the benefit of U.S. provisional application Ser. No. 60/344,654, filed Dec. 26, 2001, the disclosure of which is incorporated herein by reference in its entirety.

FIELD OF THE INVENTION

The present invention relates to non-invasive assessment of cardiac arrhythmia risk based on processing of body-surface electrocardiogram (ECG) data.

BACKGROUND OF THE INVENTION

Each year, approximately 300,000 Americans die as a result of sudden cardiac death (SCD). However, the events and mechanisms associated with arrhythmias leading to SCD are still incompletely understood. An instability of cardiac electrical excitation waves that may result in malignant cardiac polymorphic arrhythmias and fibrillation is one of the most dangerous causes of sudden cardiac death. The first preventive step towards reducing mortality from SCD is to identify individuals with unstable propagation of electrical excitation in their hearts (the risk stratification).

The cardiovascular system responds to changes in physiological conditions primarily by adjustments of the heart rate, which can be evaluated from surface measurements of ECG R-R intervals, the time stretch between consecutive R-waves. Those R waves indicate the time-intervals between two consecutive heartbeats. Such adjustments normally occur simultaneously with corresponding changes in the duration of the ECG QT intervals, which characterize the duration of electrical excitation of cardiac muscle and represent the action potential duration averaged over a certain volume of cardiac muscle (FIG. 1).

Currently, practically all major non-invasive methods of assessing an individual's susceptibility to cardiac arrhythmias include some analysis of the QT and/or RR interval spatio-temporal distribution. Indeed, the QT interval dispersion is based on the assessment of myocardial repolarization inhomogeneity (M. Zabel et al., Electrocardiographic indexes of dispersion of ventricular repolarization: an isolated heart validation study, *J. Am. Coll. Cardiol.*, 25:746–752 (1995); D. M. Mirvis, Spatial variation of QT intervals in normal persons and patients with acute myocardial infarction, *J. Am. Coll. Cardiol.*, 5:625–631 (1985)). The T wave alternans method is concerned with alternating beat-to-beat variations of the morphology of the T wave, that marks the end of a repolarization period visualized on ECG as a QT interval (Kaplan et al. U.S. Pat. No. 4,732,157, 1988; Cohen et al. No. 4,802,491, 1989). A major approach that does not include a length of the QT interval, which reflects the duration of cardiac excitation, is the heart rate variability analysis (M. Malik, Heart rate variability: Standards of measurement, physiological interpretation, and clinical use. *Circulation,* 93:1043–1065 (1996)).

Recent advances in computer technology have led to improvements in automatic analysis of heart rate and QT interval variations. It is well known now that the QT interval's spatial variability (QT dispersion) observations performed separately or in combination with the heart rate (or RR interval) variability analysis provides a tool for the assessment of individual susceptibility to cardiac arrhythmias (B. Surawicz, *J Cardiovasc Electrophysiol,* 7:777–784 (1996)). Different types of assessment of the QT and some other interval variability, both spatial and temporal, were applied to assess the susceptibility to cardiac arrhythmias as described in U.S Patents by Chamoun U.S. Pat. No. 5,020,540, 1991; Wang U.S. Pat. No. 4,870,974, 1989; Kroll et al. U.S. Pat. No. 5,117,834, 1992; Henkin et al. U.S. Pat. No. 5,323,783, 1994; Xue et al. U.S. Pat. No. 5,792,065, 1998; Lander U.S. Pat. No. 5,827,195, 1998; Lander et al. U.S. Pat. No. 5,891,047, 1999; Hojum et al. U.S. Pat. No. 5,951,484, 1999.

Dror Sadeh and coworkers (*N Engl J Med,* 317:1501–1505, (1987); *Comp. in Card.* 125–127 (1987)) studied the dependence of the mean QT interval, $<T_{QT}>$, on the mean RR interval, $<T_{RR}>$, which they presented in the form of a power function, $<T_{QT}> = \text{const} \cdot (<T_{RR}>)^\beta$ with a constant exponent $\beta$, similar to the classical Bazett equation (Bazett H. C., *Heart,* 7:353–370(1920)). They compared healthy infants and those who suffered from sudden infant death (SID) and found that the value of $\beta$ in SID babies was only half of the $\beta$ value in normal babies.

It was recently found that cardiac electrical instability can be also predicted by a combination of the QT—dispersion method observations with the ECG T-wave alternans method (Verrier et al., U.S. Pat. Nos. 5,560,370; 5,842,997; 5,921,940). This approach is somewhat useful in identifying and managing individuals at risk for sudden cardiac death. The authors report that QT interval dispersion is linked with risk for arrhythmias in patients with long QT syndrome. However, QT interval dispersion alone, without a simultaneous T wave alternans test, is said to be a less accurate predictor of cardiac electrical instability (U.S. Pat. No. 5,560,370 at column 6, lines 4–15).

Another application of the QT interval variability for prediction of sudden cardiac death is developed by J. Sarma (U.S. Pat. No. 5,419,338). He describes a method of an autonomic nervous system testing designed to evaluate the imbalances between both parasympathetic and sympathetic controls on the heart and, thus, to indicate a predisposition for sudden cardiac death.

The same author suggested that an autonomic nervous system testing procedure might be designed on the basis of the QT hysteresis (J. Sarma et al., *PACE* 10:485–491 (1988)). Hysteresis in the QT-interval during exercise and recovery was observed, and was attributed to sympathoadrenal activity in the early post-exercise period. Such an activity was revealed in the course of QT interval adaptation to changes in the RR interval and was considered to be an indicator for sudden cardiac death.

It is a well-established physiological fact that the action potential duration (APD) of a cardiac cycle depends generally on the lengths of all preceding cardiac cycles. In order to simplify the matter physiologists use a specific experimental protocol ($S_1$–$S_2$ protocol) by which this multi-parametric dependence is reduced to the primary dependence on only two parameters, the period, $T_c$, of the conditioning pacing ($S_1, S_1, \ldots S_1$, separated by the same time interval $T_c$) with which the sample was consistently stimulated (trained) prior to the test stimulus $S_2$, and the length, $T_p$, of the immediately preceding (testing) cardiac cycle, which is the time between the last stimulus $S_1$ and the following test stimulus $S_2$ (M. R. Boyett & B. R. Jewell, *J Physiol,* 285:359–380 (1978); V. Elharrar & B. Surawicz, *Am J Physiol,* 244:H782–H792 (1983)). The conditioning time or the number of conditioning stimuli, which are necessary for the consistency of the restitution results, constitutes another important and independent parameter of the medium (tissue). The physics related to excitable media points out two characteristics of the restitution process that are stability/instability indicators: the first is the slope of the restitution curve given by the dimensionless value of the partial derivative $\delta T_{QT}/\delta T_r$, and the second is the minimum training time or the characteristic transition time which is required for the wave to become periodic. The latter is similar to the conditioning time found empirically in the physiological experiments mentioned above. When this transition time is long, the medium is close to the unstable region, which closeness manifests itself by the presence of long-living oscillations of the APD and other characteristics of the wave. Such oscillations were observed in in vitro experiments (L. H. Frame & M. B. Simpson, *Circulation*, 78:1277–1287 (1988)) and in computer simulations using various models (Courtemanche et al, *Phys Rev Lett*, 14:2182–2185 (1993), SIAM J Appl Math, 56:119–142 (1996), Courtemanche, *Chaos*, 6:579–600 (1996), Y. Chernyak & J. Starobin, *Crit. Rev. Biomed. Eng.* 27:359 (1999), T. Hund & Y. Rudy, *Am J Physiol*, 279:H1869–H1879)). These fundamental physiological and physical facts constitute a general basis for the present invention.

The existing arrhythmia marker-type predictors mentioned above are accurate only under specific proarrhythmic physiological conditions, which may or may not occur in the cardiac muscle; and, therefore, they may falsely indicate an elevated arrhythmia risk (false positives) and an unnecessary electrophysiological (EP) study may ensue. The EP study is performed via cardiac catheterization, which is an invasive, expensive and somewhat hazardous procedure. Additionally, hand the existing methods possess insufficient specificity which deficiency results in missed proarrhythmic situations and lost opportunities for necessary remedial interventions. Hence, a sensitive and accurate non-invasive discrimination of proarrhythmic conditions in the heart is still a challenging diagnostic and signal-processing problem. A solution for this problem can be facilitated by the fact that computerized Holter monitors and similar devices for automatic ECG recording, its processing and obtaining QT and/or RR interval data sets are readily available and broadly accepted in clinical practice.

Accordingly, an object of the present invention is to provide a non-invasive technique for quantitatively assessing the risk of future cardiac arrhythmia in a patient.

Another object of the invention is to provide a non-invasive technique for quantitatively assessing the risk of future cardiac arrhythmia in a patient, which technique is not unduly uncomfortable or stressful for the patient.

Another object of the invention is to provide a non-invasive technique for quantitatively assessing the risk of future cardiac arrhythmia in a patient, which technique may be implemented with relatively simple equipment.

Still another object of the invention is to provide a non-invasive technique for quantitatively assessing the risk of future cardiac arrhythmia in a patient, which technique is sensitive to low risk levels of such arrhythmia.

SUMMARY OF THE INVENTION

The present invention overcomes many deficiencies of the conventional techniques and provides a method for quantitative assessment of the physiological changes in cardiac electrical conduction in cardiac ventricles that may result in the development of conduction instabilities, which manifest themselves clinically as arrhythmias. Although the present invention is generically linked to conventional arrhythmia markers and is still based on a processing of regular body surface ECG signals, it lacks the deficiencies found in the conventional approaches. The present invention introduces a continuous measure of instability that quantifies the proximity of the heart parameters to the physiological parameter region of unstable electrical propagation. When the cardiac conduction parameters belong to the unstable region or the stability boundary, even infinitesimal perturbations will grow and may lead to the development of a malignant arrhythmia. Generally, the closer the ventricle state of a subject to the unstable region the smaller perturbation is needed to initiate an arrhythmia, and, therefore, the higher the risk of arrhythmia in such a subject. Such sensitivity in defining risk stratification is impossible by means of any of the conventional, marker-type risk assessment methods described above. In particular, different individuals, who appear to have the same susceptibility to cardiac arrhythmias by a conventional method, will possess different stability measures according to the method of the present invention. The risk of an arrhythmic episode in an individual can be thus quantitatively evaluated, monitored and compared by repeated applications of the method of the present invention.

In addition to the fundamental scientific background facts mentioned in the previous section, the present invention is also based on our discoveries that (a) the control effects of the peripheral nervous system can be excluded by collecting the data under stationary or quasi-stationary conditions;

(b) a slow trend and fluctuations in the QT-RR data sets can be separated by proper processing, and two separate relationships between the trend QT and RR values and the fluctuation in the QT and RR values can be assessed and approximated by appropriate formulas;

(c) a so obtained relationship between the mean values of QT and RR intervals (the trend dependence) can be identified with the physiological (i.e., obtained in a $S_1$–$S_2$ protocol experiment) APD dependence on the time, $T_c$, between the periodic conditioning stimuli;

(d) a so obtained relationship between the QT interval fluctuation and the preceding RR interval fluctuation can be identified with the functional dependence of the difference of the last two APDs versus the difference between $T_c$ and $T_r$;

(e) the fluctuations analysis can be used to assess the slope of the restitution curve directly from non-invasively collected RR and QT interval data, and the slope can be used as a partial measure of instability (a partial arrhythmia and SCD risk measure);

(f) in the presence of the above-mentioned APD oscillations, a restitution curve must be blurred and the correlation between the fluctuations of the QT interval and the preceding RR interval must be reduced;

(g) the correlation coefficient between the fluctuations in RR and QT intervals can be used as a partial measure of stability assessed (a partial arrhythmia and SCD risk measure) by analysis of non-invasively collected RR and QT interval data sets; and (h) the product of monotonic functions of both partial stability measures constitutes a single general aggregated measure of the risk of a tested individual to develop an arrhythmia.

The present invention is based in part on the discovery that, under stationary or quasi-stationary physiological conditions, QT and/or RR interval data sets may be used to non-invasively assess major dependences of the restitution properties of the medium (in this case, cardiac muscle), which are known to determine stability of approximately periodic waves in the excitable medium. This holds true when external physiological conditions do not vary or vary sufficiently slowly so that the mean heart rate is approximately constant. In such a case the fast QT-interval adaptation controlled by sympatho-adrenal activity is completed well before the moment when the heart rate appreciably changes. Therefore, the sympatho-adrenal activity quickly becomes essentially irrelevant for the QT interval duration at a given value of constant or slowly varying mean heart rate. As a result, each QT interval depends primarily on two parameters: the mean heart rate and the preceding cardiac cycle length; and its dependence on sympatho-adrenal transients becomes negligible.

The present invention is also based in part on the discovery that the slow trend and fast temporal variations in heart rate can be separated and identified with the conditioning pacing rate and the test stimuli, respectively, in the physiological $S_1S_2$-protocol studies of restitution properties, which are generically linked with the stability of cardiac propagation. In contrast, the T wave alternans that occur below a certain physiological heart rate threshold, spatial variations (inhomogeneity) of the QT interval, a reduced heart rate variability, a reduced value of the exponent in the Basett-like formula and the QT-RR autonomic nervous system hysteresis—all of these qualitative markers may indicate the susceptibility to cardiac arrhythmias and fibrillation. However, the diagnostic value of these methods is limited because of lack of a quantitative arrhythmia measure, which would allow one to aggregate and quantify predictions acquired from each isolated arrhythmia marker.

More specifically, T-wave alternans technology is concerned with a particular arrhythmogenic mechanism (D. Rosenbaum, *J. Cardiovasc Electrophysiol*, 12:207–209 (2001)). The heart rate variability method and Sarma's QT-RR hysteresis technique are both concerned with mechanisms related to the autonomous nervous control. The QT (spatial) dispersion is linked with a specific hypothesis of the dispersion refractoriness linked to the wave fractionation mechanism (M. Zabel et al., *J Am Coll Cardiol*, 25:746–752 (1995); D. M. Mirvis, *J Am Coll Cardiol*, 5:625–631 (1985)). The idea by Sadeh et al (*N Engl J Med*, 317: 1501–1505, (1987); *Comp in Card*, 125–127 (1987)) is limited to a specific mechanism, of conduction block arising under elevated heart rates. Because of such nature of the conventional arrhythmia markers, they possess intrinsically reduced specificity. In contrast, the method of the present invention is not limited to a particular mechanism and provides a general measure of propagation stability. Therefore, the method of the present invention can be expected to possess substantially higher sensitivity and specificity as compared with conventional methods.

Technically, the method of the present invention differs from prior art by the simultaneous processing of the QT and RR temporal fluctuations and of their comparisons, while the prior art methods are either concerned with their mean values, or spatial variations or, as in the case of the heart rate variability, with temporal RR fluctuations considered without any reference to the QT fluctuations.

Based on the above, the present invention provides a quantitative method and a measure of stability of cardiac conduction. This method allows one to evaluate the actual proximity of the heart to the boundary of marginal stability and therefore to assess the risk that an arrhythmia will develop in a given subject in the future.

A first aspect of the present invention is a method of assessing risk of cardiac arrhythmia and SCD in a subject to provide a measure or measures of cardiovascular health in that subject. The method comprises the steps of:

(a) collecting at least one QT and RR interval data set from the subject during (i) a stage of gradually increasing heart rate, (ii) a stage of gradually decreasing heart rate, or (iii) both a stage of gradually increasing heart rate and gradually decreasing heart rate, or (iv) a stage of constant heart rate;

(b) separating fluctuations from slow trends in said at least one QT and RR interval data set;

(c) comparing said QT and RR fluctuations to one another to determine the relation and correlation therebetween; and (d) generating from the comparison of step (c) the first partial measure of the risk of cardiac arrhythmia in said subject, wherein a greater effect of RR interval fluctuations on the fluctuations of the immediately following QT intervals indicates greater risk of cardiac arrhythmia and SCD in said subject;

(e) generating from the comparison of step (c) the second partial measure of the risk of cardiac arrhythmia and SCD in said subject, wherein a smaller correlation between the RR interval fluctuations and QT interval fluctuations indicates greater risk of cardiac arrhythmia in said subject;

(f) generating from steps (d) and (e) an aggregated measure of the risk of cardiac arrhythmia and SCD in said subject, wherein a greater value of the first partial measure indicates a greater value of the aggregated measure and a greater value of the second partial measure indicates a greater value of the aggregated measure, and a greater value of the aggregated measure indicates a greater risk of cardiac arrhythmia and SCD.

A second aspect of the present invention is a method of assessing risk of cardiac arrhythmia in a subject, said method comprising the steps, performed on a computer system, of:

(a) providing at least one QT and RR interval data set collected from said subject during (i) a stage of gradually increasing heart rate, (ii) a stage of gradually decreasing heart rate, or (iii) both a stage of gradually increasing heart rate and gradually decreasing heart rate, or (iv) a stage of constant heart rate;

(b) separating fluctuations from slow trends in said at least one QT- and RR-interval data set;

(c) comparing said QT and RR fluctuations to one another to determine the relation and correlation therebetween; and (d) generating from the comparison of step (c) the first partial measure of the risk of cardiac arrhythmia in said subject, wherein a greater effect of RR interval fluctuations on the fluctuations of the immediately following QT intervals indicates greater risk of cardiac arrhythmia and SCD in said subject;

(e) generating from the comparison of step (c) the second partial measure of the risk of cardiac arrhythmia and SCD in said subject, wherein a smaller correlation between the RR interval fluctuations and QT interval fluctuations indicates greater risk of cardiac arrhythmia in said subject;

(f) generating from steps (d) and (e) an aggregated measure of the risk of cardiac arrhythmia and SCD in said subject, wherein a greater value of the first partial measure indicates a greater value of the aggregated measure and a greater value of the second partial measure indicates a greater value of the aggregated measure, and a greater value of the aggregated measure indicates a greater risk of cardiac arrhythmia and SCD.

Another aspect of the present invention is a computer system for assessing risk of cardiac arrhythmia in a subject, said system comprising:

(a) means for providing at least one QT and RR interval data set collected from said subject during (i) a stage of gradually increasing heart rate, (ii) a stage of gradually decreasing heart rate, or (iii) both a stage of gradually increasing heart rate and gradually decreasing heart rate, or (iv) a stage of constant heart rate;

(b) means for separating fluctuations from slow trends in said at least one QT and RR interval data set;

(c) comparing said QT and RR fluctuations to one another to determine the relation and correlation therebetween; and (d) generating from the comparison of step (c) the first partial measure of the risk of cardiac arrhythmia in said subject, wherein a greater effect of RR interval fluctuations on the fluctuations of the immediately following QT intervals indicates greater risk of cardiac arrhythmia and SCD in said subject;

(e) generating from the comparison of step (c) the second partial measure of the risk of cardiac arrhythmia and SCD in said subject, wherein a smaller correlation between the RR interval fluctuations and QT interval fluctuations indicates greater risk of cardiac arrhythmia in said subject;

(f) generating from steps (d) and (e) an aggregated measure of the risk of cardiac arrhythmia and SCD in said subject, wherein a greater value of the first partial measure indicates a greater value of the aggregated measure and a greater value of the second partial measure indicates a greater value of the aggregated measure, and a greater value of the aggregated measure indicates a greater risk of cardiac arrhythmia and SCD.

Another aspect of the present invention is a computer program product for assessing risk of cardiac arrhythmia in a subject from at least one QT and RR interval data set collected from said subject during (i) a stage of gradually increasing heart rate, (ii) a stage of gradually decreasing heart rate, or (iii) both a stage of gradually increasing heart rate and gradually decreasing heart rate, or a stage of constant heart rate, said computer program product comprising a computer usable storage medium having computer readable program code means embodied in the medium, the computer readable program code means comprising:

(a) computer readable program code means for separating fluctuations from slow trends in said at least one QT and RR interval data set;

(b) computer readable program code means for comparing said QT and RR fluctuations to one another to determine the relation and correlation therebetween; and (c) computer readable program code means for generating from the comparison of step (b) the first partial measure of the risk of cardiac arrhythmia in said subject, wherein a greater effect of RR interval fluctuations on the fluctuations of the immediately following QT intervals indicates greater risk of cardiac arrhythmia and SCD in said subject;

(d) generating from the comparison of step (b) the second partial measure of the risk of cardiac arrhythmia and SCD in said subject, wherein a smaller correlation between the RR interval fluctuations and QT interval fluctuations indicates greater risk of cardiac arrhythmia in said subject;

(f) generating from steps (d) and (e) an aggregated measure of the risk of cardiac arrhythmia and SCD in said subject, wherein a greater value of the first partial measure indicates a greater value of the aggregated measure and a greater value of the second partial measure indicates a greater value of the aggregated measure, and a greater value of the aggregated measure indicates a greater risk of cardiac arrhythmia and SCD.

The present invention is explained in greater detail in the drawings herein and the specification set forth below.

BRIEF DESCRIPTION OF THE DRAWINGS

FIG. 2A depicts a family of restitution curves, a test APD versus immediately preceding diastolic interval (DI) for different conditioning basic cycle lengths. The family represents experimental data for cat ventricular fiber and has been computed using the fitting equations provided by Elharrar & Surawicz (*Am J Physiol.* 244:H782–H792 (1983))

DETAILED DESCRIPTION OF THE PREFERRED EMBODIMENTS

Figure 1A:
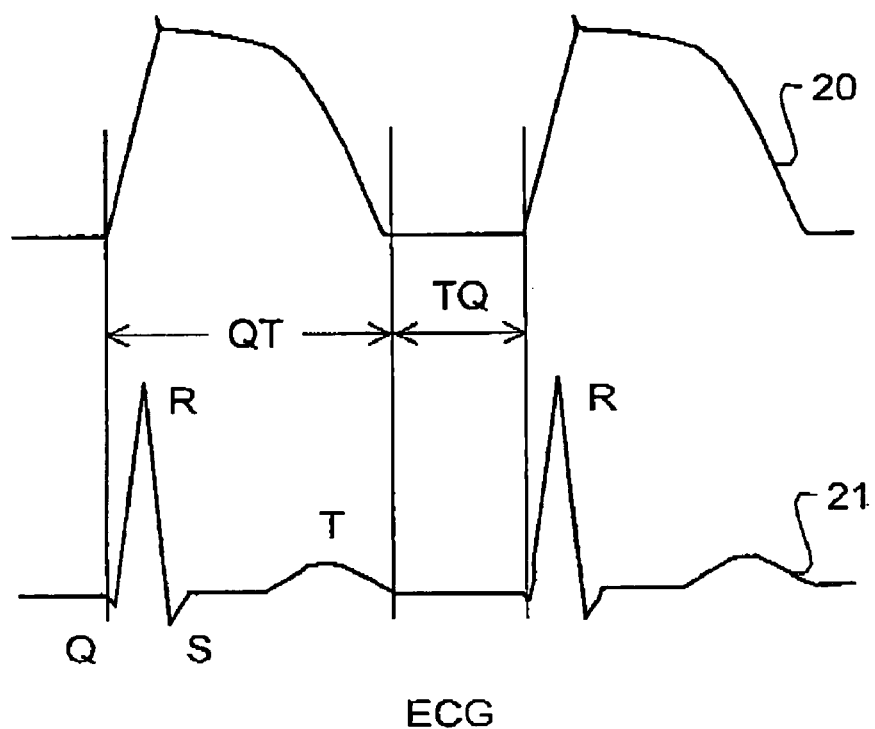
FIG. 1A is a schematic graphic representation of the action potential in cardiac muscle summed up over its volume and the induced electrocardiogram (ECG) recorded on a human's body surface.

The present invention is explained in greater detail below. This description is not intended to be a detailed catalog of all the different manners in which particular elements of the invention can be implemented, and numerous variations will be apparent to those skilled in the art based upon the instant disclosure.

As will be appreciated by one of skill in the art, certain aspects of the present invention may be embodied as a method, data processing system, or computer program product. Accordingly, certain aspects of the present invention may take the form of an entirely hardware embodiment, an entirely software embodiment, or an embodiment combining software and hardware aspects. Furthermore, certain aspects of the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

Certain aspects of the present invention are described below with reference to flowchart illustrations of methods, apparatus (systems), and computer program products. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

Computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

Computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

1. Definitions

"Cardiac arrhythmia" as used herein refers to any type of cardiac arrhythmia, including both atrial and ventricular arrhythmias. Examples include, but are not limited to, premature ventricular and supraventricular contractions, atrial flutter, ventricular and supraventricular tachycardias and ventricular and supraventricular fibrillation.

"Exercise" as used herein refers to voluntary skeletal muscle activity of a subject that increases heart rate above that found at a sustained stationary resting state.

Examples of exercise include, but are not limited to, cycling, rowing, weight-lifting, walking, running, stair-stepping, etc., which may be implemented on a stationary device such as a treadmill or in a non-stationary environment.

"Exercise load" or "load level" refers to the relative strenuousness of a particular exercise, with greater loads or load levels for a given exercise producing a greater heart rate in a subject. For example, load may be increased in weight-lifting by increasing the amount of weight; load may be increased in walking or running by increasing the speed and/or increasing the slope or incline of the walking or running surface; etc.

"Gradually increasing" and "gradually decreasing" an exercise load refers to exercise in which the subject is caused to perform an exercise under a plurality of different sequentially increasing or sequentially decreasing loads. The number of steps in the sequence can be infinite so the terms gradually increasing and gradually decreasing loads include continuous load increase and decrease, respectively.

"Intervening rest", when used to refer to a stage following increased cardiac stimulation, refers to a stage of time initiated by a sufficiently abrupt decrease in heart stimulation (e.g., an abrupt decrease in exercise load) so that it evokes a clear sympatho-adrenal response. Thus, an intervening rest stage is characterized by a rapid sympatho-adrenal adjustment (as further described in Example 6 below), and the inclusion of an intervening rest stage precludes the use of a quasi-stationary exercise (or stimulation) protocol (as further described in Example 7 below).

"Hysteresis" refers to a lagging of the physiological effect when the external conditions are changed.

"Electrocardiogram" or "ECG" refers to a continuous or sequential record (or a set of such records) of a local electrical potential field obtained from one or more locations outside the cardiac muscle. This field is generated by the combined electrical activity (action potential generation) of multiple cardiac cells. The recording electrodes may be either subcutaneously implanted or may be temporarily attached to the surface of the skin of the subject, usually in the thoracic region. An ECG record typically includes the single-lead ECG signal that represents a potential difference between any two of the recording sites including the site with a zero or ground potential.

"Quasi-stationary conditions" refer to any situation in which a gradual change in the external conditions and/or the physiological response it causes occurs slower than any corresponding adjustment due to sympathetic/parasympathetic and hormonal control. If the representative time of the external conditions variation is denoted by $\tau_{ext}$, and $\tau_{int}$ is a representative time of the fastest of the internal, sympathetic/parasympathetic and hormonal control, then "quasi-stationary conditions" indicates $\tau_{ext} \gg \tau_{int}$ (e.g., $\tau_{ext}$ is at least about two, three, four or five times greater than $\tau_{int}$). Abrupt changes in exercise load may be either quasi-stationary or non-quasi-stationary. "A non-quasi-stationary abrupt change" refers to a situation opposite quasi-stationary conditions corresponding to a sufficiently fast change in the external conditions as compared with the rate sympathetic/parasympathetic and hormonal control—that is, it requires that $\tau_{ext} \ll \tau_{int}$ (e.g., $\tau_{ext}$ is at least about two, three, for our five times less than $\tau_{int}$). "A quasi-stationary abrupt change" refers to a relatively fast change in exercise load that is nonetheless quasi-stationary-, for example, because the change is preceded by a sufficiently high exercise load such that a slower, quasi-stationary recovery period is observed.

"QT and RR data set" refers to a record of the time course of an electrical signal comprising action potentials spreading through cardiac muscle. Any single lead ECG record incorporates a group of three consecutive sharp deflections usually called a QRS complex and generated by the propagation of the action potential's front through the ventricles. In contrast, the electrical recovery of ventricular tissue is seen on the ECG as a relatively small deflection known as the T wave. The time interval between the cardiac cycles (i.e., between the maxima of the consecutive R waves) is called a RR interval, while the action potential duration (i.e., the time between the beginning of a QRS complex and the end of the ensuing T wave) is called a QT interval. Alternative definitions of these intervals can be equivalently used in the framework of the present invention. For example, an RR interval can be defined as the time between any two similar points, such as the similar inflection points, on two consecutive R waves, or in any other manner to measure cardiac cycle length. A QT interval can be defined as the time interval between the peak of the Q wave and the peak of the T wave. It can also be defined as the time interval between the beginning (or the center) of the Q wave and the end of the ensuing T wave defined as the point on the time axis (the base line) at which it intersects with the linear extrapolation of the T wave's falling branch and started from its inflection point, or in any other manner to measure action potential duration. An ordered set of such interval durations simultaneously with the time instants of their beginnings or ends which are accumulated on a beat to beat basis or on any given beat sampling rate basis form a corresponding QT and RR interval data set. Thus, a QT and RR interval data set will contain two QT interval related sequences $\{T_{QT,1}, T_{QT,2}, \ldots, T_{QT,n}\}$ and $\{t_1, t_2, \ldots, t_n\}$, and will also contain two RR-interval related sequences $\{T_{RR,1}, T_{RR,2}, \ldots, T_{RR,n}\}$ and $\{t_1, t_2, \ldots, t_n\}$ (the sequence $\{t_1, t_2, \ldots, t_n\}$ may or may not exactly coincide with the similar sequence in the QT data set).

In the following definitions, $C[a,b]$ shall denote a set of continuous functions $f(t)$ on a segment $[a,b]$. $\{t_i\}$, $i=1, 2, \ldots, N$, denotes a set of points from $[a,b]$, i.e. $\{t_i\}=\{t_i: a \leq t_i \leq b, i=1, 2, \ldots, N\}$ and $\{f(t_i)\}$, where $f \in C[a,b]$, denotes a set of values of the function $f$ at the points $\{t_i\}$. In matrix operations the quantities $\tau = \{t_i\}$, $y = \{f(t_i)\}$, are treated as column vectors. $E_N$ shall denote an N-dimensional metric space with the metric $R_N(x,y)$, $x,y \in E_N$. ($R_N(x,y)$ is said to be a distance between points x and y.) A (total) variation $$\overset{b}{\underset{a}{V}}[F]$$

is defined for any absolutely continuous function F from $C[a,b]$ as the integral (a Stieltjes integral)

$$\overset{b}{\underset{a}{V}}[F(t)] \equiv \int_a^b |dF(t)| = \int_a^b |F'(t)|dt. \quad \text{(D.1)}$$

For a function F monotonic on segment $[a,b]$ its variation is simply $|F(a)-F(b)|$. If a function F(t) has alternating maxima and minima, then the total variation of F is the sum of its variations on the intervals of monotonicity. For example, if the points of minima and maxima are $x_1=a, x_2, x_3, \ldots, x_k=b$ then $$\overset{b}{\underset{a}{V}}[F(t)] = \sum_{i=1}^{k-1} |F(x_i) - F(x_{i+1})|. \quad \text{(D.2)}$$

A total variation of a data set: If data points are $\{y_i\}=\{y_1, y_2, \ldots, y_n\}$ then the total variation of the data set is defined by the equation $$\overset{b}{\underset{a}{V}}\{y_i\} = \sum_{k=1}^{n-1} |y_{k+1} - y_k| \quad \text{(D.3)}$$

Fitting (best fitting): Let $\bar{C}[a,b]$ be a subset of $C[a,b]$. A continuous function $f(t)$, $f \in \bar{C}[a,b]$ is called the (best) fit (or the best fitting) function of class $\bar{C}[a,b]$ with respect to metric $R_N$ to a data set $\{x_i, t_i\}$ (i=1, 2, \ldots, N) if $$R_N(\{f(t_i)\}, \{x_i\}) = \min_{f \in \bar{C}[a,b]} \quad \text{(D.4)}$$

The minimum value of $R_N$ is then called the error of the fit. The functions $f(t)$ from $\bar{C}[a, b]$ will be called trial functions.

In most cases $E_N$ is implied to be an Euclidean space with an Euclidean metric.

The error $R_N$ then becomes the familiar mean-root-square error. The fit is performed on a subset $\bar{C}[a, b]$ since it usually implies a specific parametrization of the trial functions and/or such constraints as the requirements that the trial functions pass through a given point and/or have a given value of the slope at a given point.

A smoother function (comparison of smoothness): Let $f(t)$ and g(t) be functions from $C[a,b]$ that have absolutely continuous derivatives on this segment. The function $f(t)$ is smoother than the function g(t) if $$\overset{b}{\underset{a}{V}}[f(t)] \leq \overset{b}{\underset{a}{V}}[g(t)], \quad \text{(D.5)}$$

and $$\overset{b}{\underset{a}{V}}[f'(t)] \leq \overset{b}{\underset{a}{V}}[g'(t)], \quad \text{(D.6)}$$

where the prime denotes a time derivative, and a strict inequality holds in at least one of relations (D.5) and (D.6).

A smoother set: A set $\{x_i, t_i\}$ (i=1, 2, ..., N) is smoother than the set $\{x'_j, t'_j\}$ (j=1, 2, ..., N') if the former can be fit with a smoother function $f(t)$ of the same class within the same or smaller error than the latter. One can prove that a smoother data set has a smaller total variation.

Smoothing of a data set: A (linear) transformation of a data set $(x,t) \equiv \{x_i, t_i\}$ (i=1, 2, ..., N$_0$) into another set $(y\tau) \equiv \{y_j, \tau_j\}$ (j=1, 2, ..., N$_1$) of the form $$y = A \cdot x, \quad t = B \cdot t,  \quad\quad (D.7)$$

where A and B are $N_1 \times N_0$ matrices, is called a smoothing if the latter set is smoother than the former. One can refer to $\{y_j, \tau_j\}$ as a smoothed set.

A "trend" on a data segment is a data set generally obtained from the raw data segment by low-pass filtering under the restriction that the deviations from the resulting trend have zero sum. In a particular implementation herein, a trend is assessed as the smoothest data set obtained by fitting the raw data on the segment with a lowest degree polynomial (linear or quadratic, the latter being used when the data set encompasses a single extremum, i.e. a minimum or a maximum). The total variation of the trend is always much smaller than the total variation of the raw data segment.

A "stationary data segment" is a data segment with a negligible variation in its trend.

A "slow trend" is a trend with a small but not negligible variation. A trend obtained under the quasi-stationary protocol (see example 7) is a slow trend. A duration of a stage during which the data incorporating a slow trend are collected must be approximately an order of magnitude (e.g., at least about two, three, four, five or ten times) longer than the average duration (~1 minute) of the heart rate adjustment after an abrupt stop of exercise from a peak load rate (typically from 120 to 150 beat/min) to the rest rate (typically from 50 to 70 beat/min).

A "fluctuation" or "fast fluctuation" of a QT or RR interval on a data segment as used herein refers to a set of zero sum deviations from a QT (or, respectively, RR) slow trend corresponding to this particular data segment. A traditional measure of fluctuations is the standard root-mean-square deviation (STD). A typical value of STD for QT (or RR) interval fluctuations is of an order of magnitude (e.g., at least about two, three, four, five or ten times) smaller than the total variation of the QT (or, respectively, RR) interval trend during the entire load stage under quasi-stationary conditions.

"Instantaneous restitution dependences" refer to curves representing QT-interval fluctuations versus RR-interval fluctuations, fluctuations being understood as the zero sum deviations from the corresponding QT and RR slow trends.

2. Restitution Properties

Figure 1B:
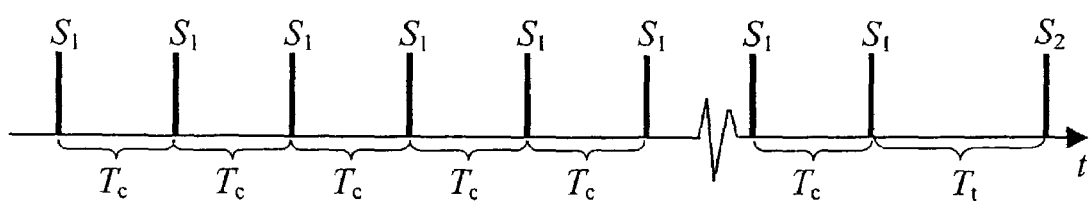
FIG. 1B shows a typical sequence of n+1 stimuli corresponding to the S1–S2 protocol. The first n stimuli are equally spaced with a basic cycle length $T_c$, and comprise a sequence of conditioning stimuli. The time between the last, n-th conditioning stimulus and the (n+1)-th, test stimulus is $T_t$. The variation of the test cycle length is defined as $T_t-T_c$.
Figure 2B:
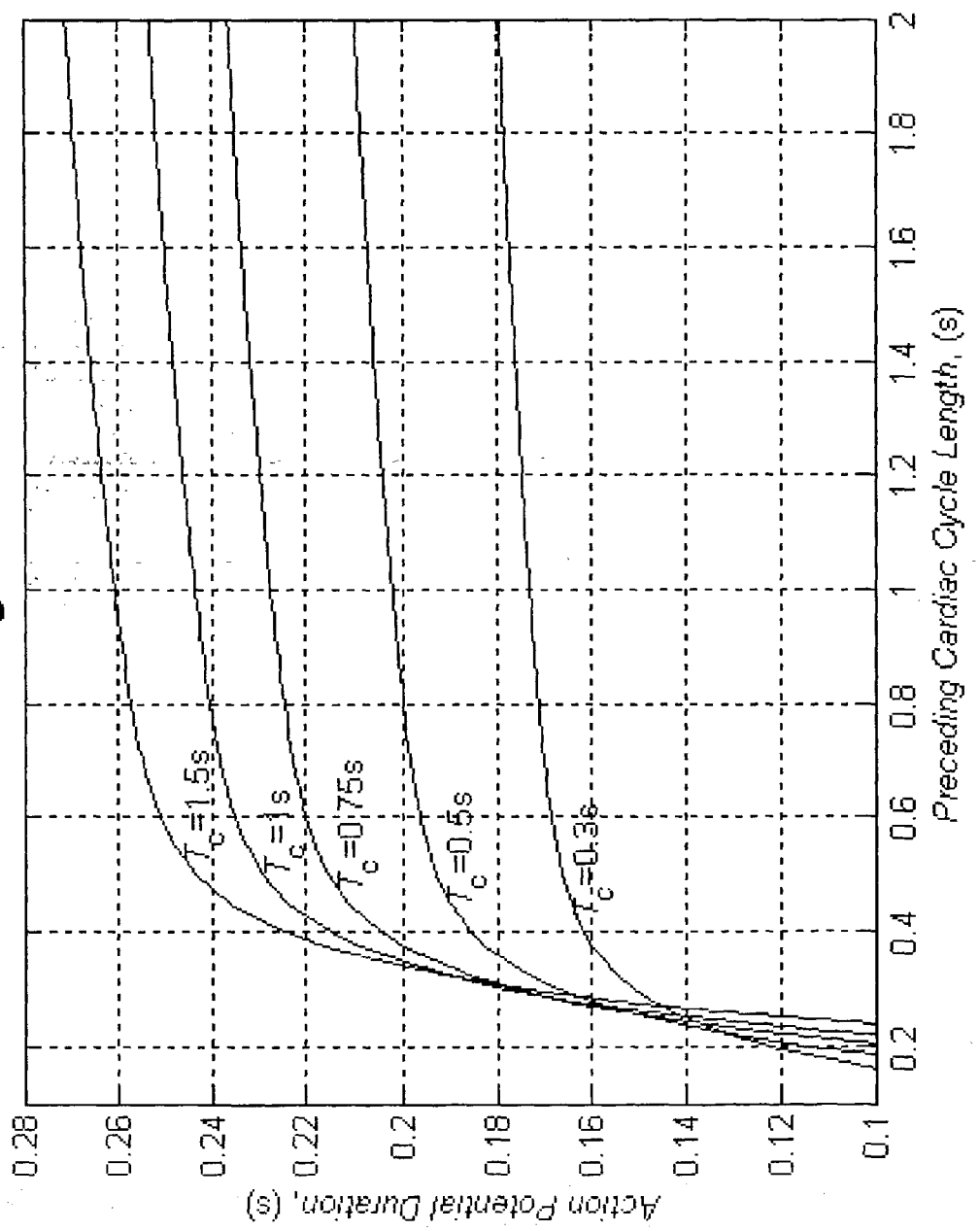
FIG. 2B depicts the same family as FIG. 2A but represented via more convenient coordinates, a test APD versus immediately preceding cycle length (or RR-interval) for different basic conditioning cycle lengths.
Figure 2C:
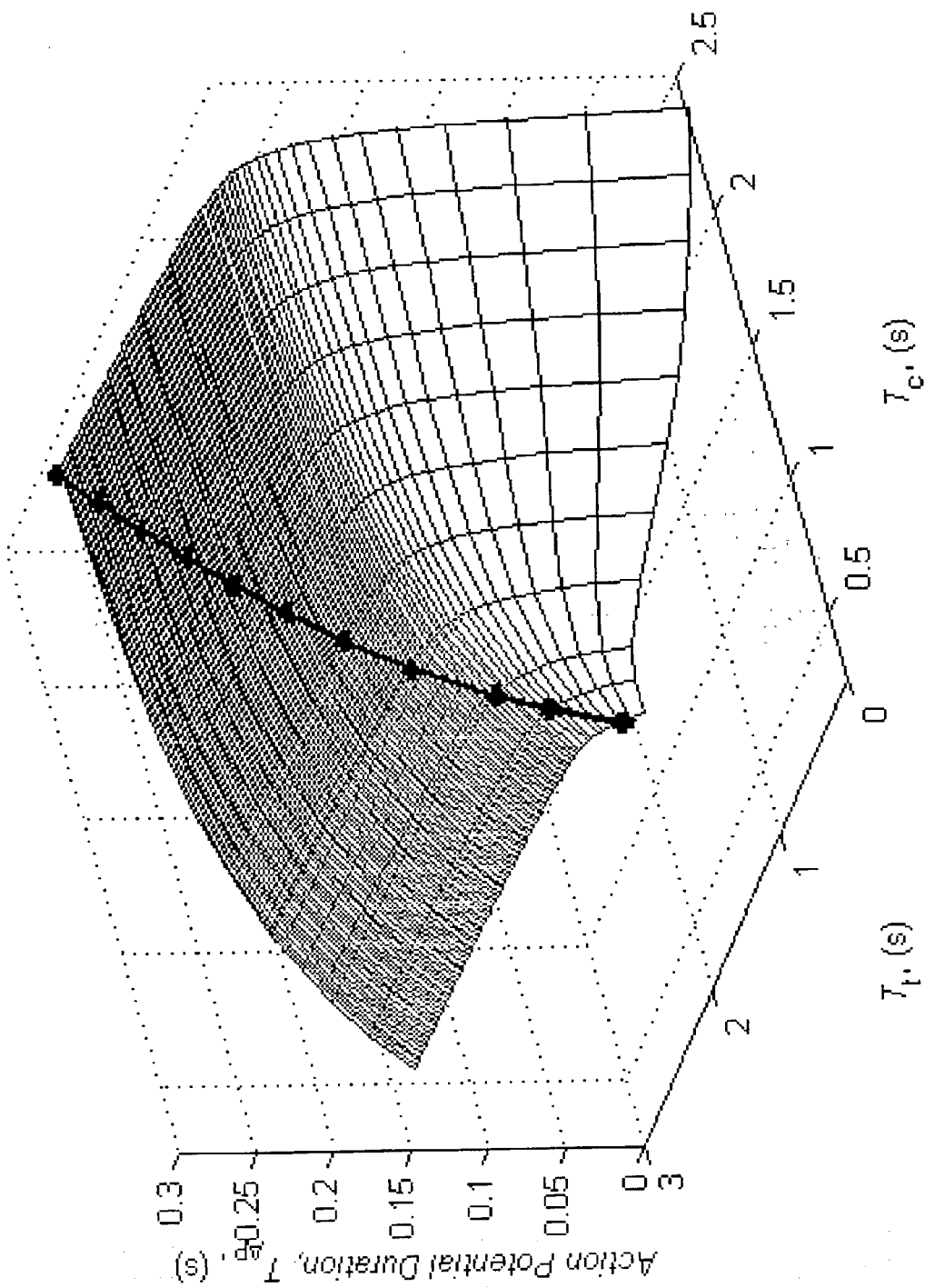
FIG. 2C depicts a three-dimensional view of the restitution properties shown in FIGS. 2A and 2B but plotted as a test APD versus basic conditioning cycle length and an immediately preceding (test) cycle length.
Figure 2D:
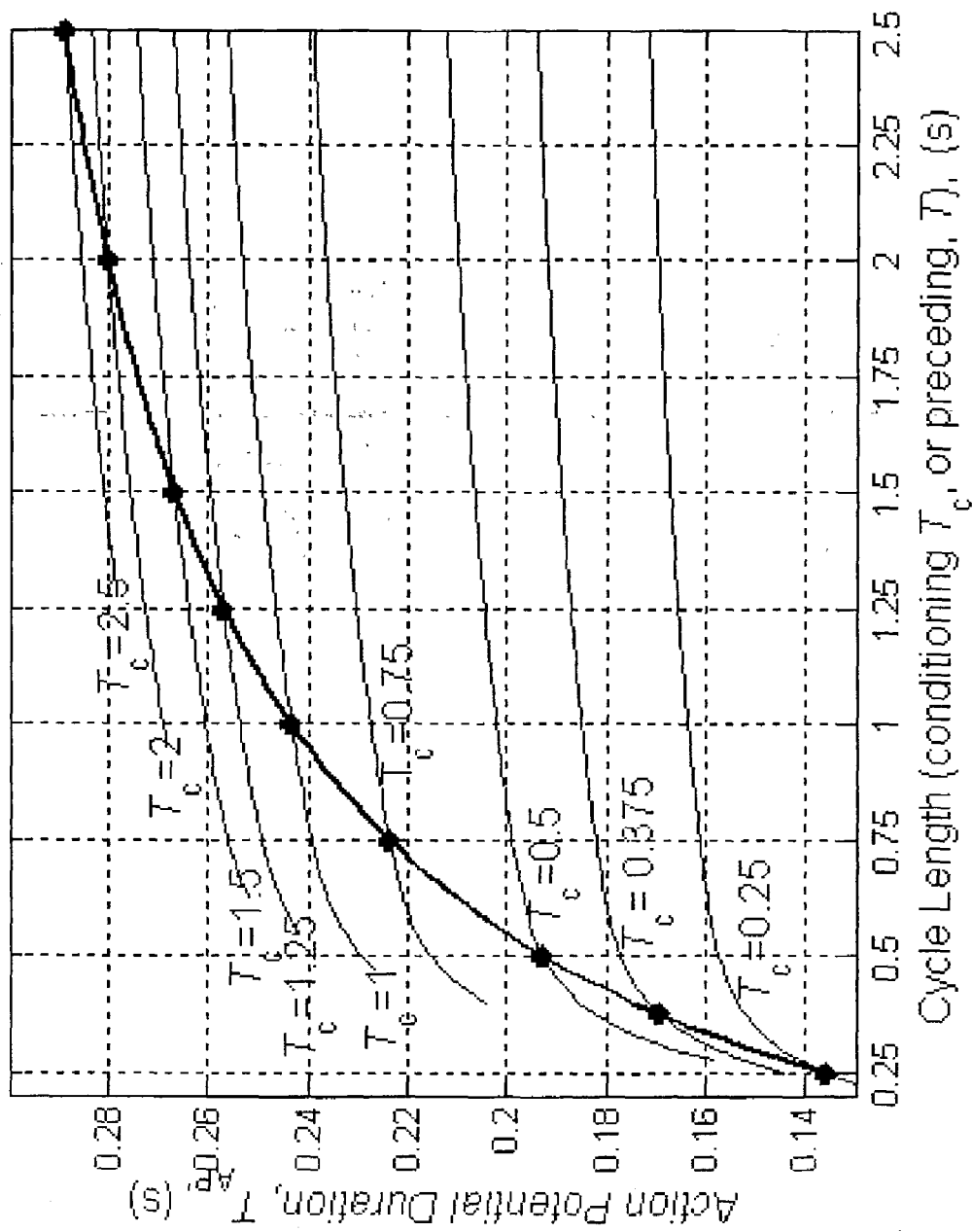
FIG. 2D depicts another three-dimensional view of the same restitution properties plotted as a test APD versus a basic conditioning cycle length and a variation of the immediately preceding cycle length (the difference between the test cycle length and the conditioning cycle length).

FIG. 1 illustrates the correspondence between the temporal phases of the periodic action potential (AP, upper graph, 20) generated inside cardiac muscle and summed up over its entire volume and the electrical signal produced on the body surface and recorded as an electrocardiogram (ECG, lower graph, 21). The figure depicts two regular cardiac cycles. During the upstroke of the action potential the QRS-complex is formed. It consists of three waves, Q, R, and S, which are marked on the lower panel. The recovery stage of the action potential is characterized by its fall off on the AP plot and by the T-wave on the ECG plot. One can see that the action potential duration (APD) is well represented by the time between Q and T waves and is conventionally defined as the QT interval, measured from the beginning of the Q wave to the end of the following T wave. The time between consecutive R-waves (RR interval) represents the duration of a cardiac cycle, while its reciprocal value represents the corresponding instantaneous heart rate. We shall identify below the RR interval (duration) with the cycle length and QT interval (duration) with the APD.

Restitution curve and a restitution function. The capability of myocardial tissue to recover after a depolarization and conduct the ensuing action potential wave is reflected in restitution properties of the tissue. When incompletely recovered tissue is stimulated, the ensuing action potential is less pronounced and has a shorter APD, which traditionally serves as a measure of restitution properties. In vitro measurements of restitution properties of excitable, in particular cardiac, tissue reveal that the duration of a given, say (n+1)-th, action potential $T_{AP}^{n+1}$, generally depends on all preceding cardiac cycle lengths, $T_1, T_2, \ldots, T_{n+1}$. This can be expressed as a general restitution relation $$T_{AP}^{n+1} = r_g(T_1, T_2, \ldots, T_{n+1}) \quad\quad (R.1)$$

The n-th action, $T_{AP}^{n+1}$, will be referred to as the test action potential, while the cardiac cycle immediately preceding it will be referred to as the test cardiac cycle. The effect of the test cardiac cycle length, $T_{n+1}$, on the test APD is the most pronounced. The effect of a more remote cardiac cycle, $T_k$, diminishes as its separation, |n+1−k|, from the test cycle increases. However, a summed up effect of many remote cycles can be quite significant. These two major effects are taken into consideration in traditional in vitro restitution measurements using a special $S_1$–$S_2$ protocol illustrated in FIG. 1B. According to this $S_1$–$S_2$ protocol the tissue is first trained (conditioned) by a periodic pacing sequence of n identical stimuli $S_1$ with a period $T_c$ until all observed characteristics such as APD become periodic with the stimulation period $T_c$. Next, after the last (nth) conditioning stimulus $S_1$ a test stimulus, $S_2$, is applied with a variable delay of $T_t$ (Bass B. G. Am. J. Physiol. 228:1717–1724, (1975)). Under such a protocol the APD and other quantitative characteristics of the last, (n+1)th, test wave in the $S_1$, $S_1, \ldots, S_1$–$S_2$ sequence become functions of the conditioning cycle length, $T_c$, and the test cycle length, $T_t$. In the case of APD such a function is called a restitution function $r(T_t, T_c)$, that can be expressed via the general restitution function, $r_g$, as follows $$T_{AP}^{n+1} = r_g(T_c, T_c, \ldots, T_c, T_t) \equiv r(T_c, T_t) \quad\quad (R.2)$$

Since APD is represented by the QT interval and the cycle lengths is represented by the RR interval, the restitution function in the ECG terms can be presented in the form $$T_{QT}^t = r(T_{RR}^c, T_{RR}^t), \quad\quad (R.3)$$

where $T_{RR}^t$ and $T_{RR}^c$ are test and conditioning RR intervals, respectively. It is important that the first and second arguments of the restitution function r(,) are independent, since one can set experimentally an arbitrary delay between the $S_2$ and $S_1$ stimuli. When the test cycle length, $T_t$, is equal to the conditioning cycle length, $T_c$, the ensuing APD must coincide with the conditioning APD; so we have $$T_{QT}^c = r(T_c, T_c) = r(T_{RR}^c, T_{RR}^c). \quad\quad (R.4)$$

The resting time prior to a new cardiac cycle is measured by a diastolic interval $T_{DI}$ and hence the restitution properties are often presented as a dependence of APD on $T_c$ and the immediately preceding $T_{DI}$ (Bass B. G. *Am. J. Physiol.* 228:1717–1724, (1975)). Since RR interval represents the duration of the entire cardiac cycle, we have for an arbitrary kth cycle $$T_{RR}^k = T_{DI}^k + T_{QT}^k. \tag{R.5}$$

In particular, the test DI is preceded by the steady state and conditioning action potential. Therefore we have $$T_{RR}^t = T_{DI}^t + T_{QT}^c. \tag{R.6}$$

According to Eq-s (R.4), (R.6) and (R.3) the restitution properties can be equivalently represented as $$T_{QT}^t = r(T_{RR}^c, T_{DI}^t + T_{QT}^c) = r(T_{RR}^c, T_{DI}^t + r(T_{RR}^c, T_{RR}^c)) \equiv R(T_{RR}^c, T_{DI}^t). \tag{R.7}$$

The function $R(T_t, T_c)$ is the most traditional form of the restitution function for in vitro experiments although for clinical measurements the function $r(.,.)$ is preferable (Bass B. G. *Am. J Physiol.* 228:1717–1724, (1975); M. R. Boyett & B. R. Jewell, *J Physiol*, 285:359–380 (1978); V. Elharrar & B. Surawicz, *Am J Physiol*, 244:H782–H792 (1983)). Both the degree to which the real cardiac conduction obeys a restitution relation as well as some quantitative characteristics of the restitution curve play crucial roles in the stability of cardiac conduction.

A representation of the restitution curve via clinically accessible measurements of QT and RR interval time series. The rate dependence of the restitution properties creates serious difficulties for their noninvasive clinical assessment since it appears necessary to apply an externally controlled $S_1, S_1, \ldots, S_1 - S_2$ pacing sequence, which is usually done only via an invasive procedure.

We shall discuss herein how measuring and comparing the RR and QT-interval fluctuations at constant (or almost constant) heart rate allows one to noninvasively assess the actual, heart rate dependent restitution function. The idea of a noninvasive clinical measurement of the restitution curve is based on the fact that during periods of stationary or quasi-stationary cardiac activity the variations of the cardiac rhythm can be separated into slow changes of the average cardiac cycle length and fast beat-to-beat fluctuations. The former may look like systematic variations while the latter appear to be random. One can liken a pacing sequence generated by the natural cardiac pacemaker unit, the sino-atrial (SA) node to the above $S_1, S_1, ,S_1-S_2$ sequence as follows. Under steady conditions the SA node generates pacing signals which are approximately periodic, with the cycle length fluctuating around the average conditioning value $T_c$. The cumulative properties of the last wave in a sequence stimulated by the sino-atrial node will depend on the mean heart rate very similar to the dependence on the rate of the conditioning pacing. On the other hand, there are always some fluctuations of the cardiac cycle length (unless the heart is driven by an implanted pacemaker). Due to such fluctuations the length of a cardiac cycle immediately preceding any given action potential varies and is quite similar to experimental variations of the test, $S_1-S_2$, interval. This means that the natural pacing sequence $S_1, S_2, \ldots, S_n-S_{n+1}$ can be viewed very much as the laboratory sequence $S_1$, $S_1, \ldots, S_1-S_2$, with the only difference that the conditioning cycle length is not strictly constant but fluctuates.

Consider a stationary physiological situation when the preceding RR intervals $T_1, T_2, \ldots, T_n$, fluctuate about the mean value $<T_k> \equiv T_c$, so one can write $$T_k = T_c + \delta T_k, \quad <\delta T_k> = 0 \tag{R.8}$$

Substituting Eq.(R.8) into (R.1) one has $$T_{AP}^{n+1} = r_g(T_c + \delta T_1, T_c + \delta T_2, \ldots, T_c + \delta T_n, T_{n+1}) \tag{R.9}$$

Since the fluctuations $\delta T_k$ are small, one can expand this relation into a Taylor series and obtain within the first order $$T_{AP}^{n+1} = r_g(T_c, T_c, \ldots, T_c, T_{n+1}) + \sum_{k=1}^{n} \frac{\partial r_g(T_c, T_c, \ldots, T_c, T_{n+1})}{\partial T_k} \delta T_k. \tag{R.10}$$

The experimentally meaningful observable values are given by the expected (mean) values of random variables; so one needs to average relation (R.10) and evaluate $$\langle T_{AP}^{n+1} \rangle.$$

Taking into account the fact that $<\delta T_k>=0$ and using Eq. (R.2), finally we find $$\langle T_{AP}^{n+1} \rangle = r_g(T_c, T_c, \ldots, T_c, T_{n+1}) \equiv r(\langle T_k \rangle, T_{n+1}). \tag{R.11}$$

Averaging implies only the first n cardiac cycles and does not involve the (n+1)th test one. The meaning of Eq. (R.11) can be better understood if we recall that $$\langle T_{AP}^{n+1} \rangle = \langle T_{AP} \rangle + \delta T_{AP}^{n+1}$$

and $T_{n+1} = T_c + \delta T_{n+1}$ so Eq. (R.11) can be written as a relationship between the trends and the fluctuations in the form $$\delta T_{AP}^{n+1} = r(T_c, T_c + \delta T_{n+1}) - \langle T_{AP} \rangle \tag{R.12}$$

Thus, the restitution properties of the excitable medium depend on both the trend values and fluctuations of the APD and cardiac cycle length. Equation (R.12) is the basis for the proposed technology because APD ($T_{AP}$) and cardiac cycle length ($T_c$) can be evaluated noninvasively as the duration (length) of the QT-and RR-interval, respectively. Therefore, Eq. (R.12) can be expressed via noninvasively measurable quantities as follows $$\delta T_{QT}^{n+1} = r(\langle T_{RR}^c \rangle, \langle T_{RR}^c \rangle + \delta T_{RR}^c) - \langle T_{RR}^c \rangle \qquad (R.13)$$

It is important that the last fluctuation is not assumed to be small. According to Eq.(R.13) restitution properties depend on both the trend values and fluctuations of RR- and QT-interval. This suggests that various characteristics of the restitution curve such as the slope and higher derivatives can be evaluated from the simultaneous measurements of the beat-to-beat fluctuations (small deviations from the average) of the RR and QT intervals. The first step is the determination of the trend and fluctuations, or the separation of the trend and fluctuations from the original data time series. The sufficient condition so that the trend and fluctuations can be unambiguously separated is that heart rate must vary very little during each period of data collection so that the system can be considered as remaining in one state corresponding to a constant heart rate.

These conditions are satisfied with high precision during a quasi-stationary exercise protocol if the data collection time segments are not too long—e.g. from 15 s to 60 s. This is because the conditions of quasi-stationarity include the requirement that the exercise load is sufficiently large to ensure the RR-interval fluctuations to be sufficiently small and also the requirement that the heart rate varies slowly so the total variation of the heart rate is also sufficiently small.

3. Stability (Arrhythmia Risk) Criteria

From a physical point of view any transition from one cardiac rhythm to another is a manifestation of instability of the periodic action potential wave in the heart. In particular, an arrhythmia generally evolves from unstable propagation of an action potential. Therefore, it is important to find stability measures that can be clinically assessed, can be compared with certain empirical standards and can thereby serve as quantitative criteria of the stability/instability of cardiac conduction and the risk of the assessed individual to develop an arrhythmia.

The first partial stability measure and criterion. It has been established for various models (see, e.g., J. Rinzel & J. Keller Biophys J 13:1313–1337 (1973); Feldman, Y. Chernyak & R Cohen, Phys Rev, E57:7025–7040 (1998); Y. Chernyak J. Starobin & R. Cohen, Phys Rev E58: R4108–R4111 (1998)) that a stationary propagation of a periodic action potential wave is possible only if the wave parameters correspond to the stable branch of the dispersion curve on which the propagation velocity decreases with the increase of the wave's frequency. This is a necessary condition for a stable stationary propagation. As also shown in Y. Chernyak & J. Starobin (Crit Rev Biomed Eng, 27:359–414 (1999)), the stable branch of the dispersion curve is separated from the unstable branch by the point with vertical slope. Using the technique developed by Y. Chernyak J. Starobin & R. Cohen (Phys Rev E58: R4108–R4111 (1998)) one can prove that at the point of marginal stability the restitution function satisfies the requirement $$s \equiv \frac{\partial r(T_{RR}^c, T_{RR}^t)}{\partial T_{RR}^t} \equiv r_t'(T_{RR}^c, T_{RR}^t) = \infty, \qquad (S.1)$$

where subscript, t, indicates that the derivative is partial and is taken with respect to the second variable, the test RR-interval. The underlying general idea is that essentially no stationary propagation of a periodic wave is possible unless the wave parameters correspond to the stable portions of the dispersion and restitution curves. When the propagation becomes non-stationary, one may expect these instabilities to be a precursor for the development of complex rhythms (arrhythmias). According to Eq. (S.1), a periodic wave propagates in an unstable manner if the derivative, $r_t'$, is infinite.

Courtemanche, Glass, and Keener [Phys. Rev. Lett., 14, 2182–2185(1993), SIAM J. Appl. Math., 56, 119–142(1996)] suggested that restitution properties determine the conduction stability and developed an approximate theory. The stability condition for a period doubling of the electrical activity in a single myocyte was found by Glass and coworkers, (Guevara et al Science, 214: 1350–1353 (1981), Glass 1984). The criterion for such an instability can also be expressed in terms of the restitution curve slope, s, as $$s = r_t'(T_{RR}^c, T_{RR}^c) = 1, \qquad (S.2)$$

It is important to note that the slope $r_t'$ in a healthy subject at a normal heart rate is fairly small, of the order of 0.1. This is because the QT interval is always considerably shorter that the RR-interval. Therefore, both conditions (S.1) and (S.2) indicate that the slope is significantly greater than what is typical for a normal individual. These equations indicate that when the derivative becomes sufficiently large, one should expect the development of instabilities. A supporting evidence was found using a particular model of cardiac tissue, which demonstrated that near the stability boundary complex, quasi-periodic rhythms develop (I. Schwartz, I. Triandaf., J. Starobin & Y. Chernyak, Phys Rev E61: 7208–7211, (2000)). Thus, the value of the derivative $r_t'$ is useful as stability measure for periodic cardiac waves.

Thus, stability criteria obtained in different approaches can be expressed via the stability measure, the value of the partial derivative $r_t'$. These results indicate that the slope $s = r_t'$ constitutes a major stability measure similar to the Reynolds number in hydrodynamics or the Euler number in convection theory. When the Reynolds number of a flow reaches a certain critical value, a transition between laminar and turbulent mode occurs. In hydrodynamics, the critical value depends on geometry, and may be somewhat different for streams with circular or square cross sections. The particular criterion value of the Reynolds number is usually found from experiment, especially when geometry is complex. However, the notion of a dimensionless Reynolds number provides a general criterion of stability. Similarly, the dimensionless slope $s = r_t'(T_c, T_c)$ can be used as a dimensionless stability measure. The requirement of cardiac rhythm stability at a given mean cardiac cycle length $T_{RR}$ will be expressed in the form $$s = r_t'(\overline{T}_{RR}, \overline{T}_{RR}) < s_{crit}, \qquad (S.3)$$

where $\overline{T}_{RR} = \langle T_{RR} \rangle$ is the mean value of the stationary or quasi-stationary RR interval and $s_{crit}$ is a critical value of the slope, s, which can be evaluated theoretically and/or found from experiments and observations. The fact that both arguments in $r_1'(\overline{T}_{RR}, \overline{T}_{RR})$ are equal follows from the derivation of equation (F.19) below. Eq.(S.3) has a typical structure of a stability criterion, which compares an actual value of the stability measure and its critical value. The stability criterion (S.3) is invariant with respect to an arbitrary monotonic (growing) transformation $\{F:[r_t', s_{crit}] \rightarrow [F(r_t'), F(s_{crit})]\}$ with a monotonically growing function $F(.)$.

The second partial stability measure and criterion. Various stability studies indicate that prior to the destruction of the wave by instability and the transition into another mode the wave shows some long-living oscillations of APD and other characteristics of the wave. Such oscillations were observed in in vitro experiments (L. H. Frame & M. B. Simpson, *Circulation*, 78:1277–1287 (1988)) and in computer simulations using various models (Courtemanche et al, *Phys Rev Lett*, 14:2182–2185 (1993), SIAM J Appl Math, 56:119–142 (1996), Courtemanche, *Chaos*, 6:579–600 (1996), Y. Chernyak & J. Starobin, *Crit. Rev. Biomed. Eng.* 27:359–414 (1999), T. Hund et al, *Am J Physiol*, 279: H1869–H1879(2000)). The physical nature of such APD oscillations was interpreted by Y. Chernyak & J. Starobin (*Crit. Rev. Biomed. Eng.* 27:359–414 (1999) as a manifestation of long-living eigen-oscillations that indicate a propagation instability and are necessary predecessors of a propagation regime change. It appears very difficult, practically impossible, to directly observe such oscillations clinically due to a variety of serious reasons. However, some secondary necessary effects of such oscillations can be directly observed. In particular, the oscillations of APD must blur and may fully or in part destroy the restitution dependence.

Such short-term blurring must manifest itself by a reduction of the dimensionless correlation coefficient between the fluctuations of the APD and the preceding RR interval. A very similar reduction of correlation between APD and the test cycle length duration in their in vitro restitution measurements was indeed observed by Elharrar & Surawicz (*Am J Physiol*, 244:H782–H792 (1983)). In a context unrelated to the test wave stability they showed that the fast component of the restitution dependence may become apparently random under high conditioning pacing rate, although they did not comment on the possible stability implications.

A dimensionless correlation coefficient, $k_{QR}$, between QT and RR interval fluctuations is a convenient criterion for assessing this effect $$k_{QR} = \frac{\frac{1}{N}\sum_{k=1}^{N} \delta T_{QT}^k \delta T_{RR}^k}{\sigma_{QT}\sigma_{RR}}, \quad (S.4)$$

where $\sigma_{QT}$ and $\sigma_{RR}$ are the estimates for standard deviations of QT and RR interval, respectively. Notice that in Eq-s (R1) and (R.9)-(R.11) the quantity $T_k$ is the length of a cardiac cycle which immediately precedes k-th action potential with the APD, $T_{AP}^k$. Accordingly, $T_{QT}^k$ is the QT interval immediately following the k-th RR interval with the duration $T_{RR}^k$. Therefore, the correlation coefficient given by Eq. (S.4) satisfies the causality requirement and may indeed reflect the degree of direct short-term causal relation between $T_{RR}^k$ and $T_{QT}^k$. The corresponding partial stability criterion will have the form $$k_{QR} > \kappa_{crit}, \quad (S.5)$$

where $\kappa_{crit}$ is a critical value of the correlation coefficient slope, which can be assessed empirically using clinical data and test results.

The third partial stability measure and criterion. A more general characterization of the correlation between two observed time series of RR and QT intervals is the cross-correlation coefficient defined as $$k_{RR}^{QT}(j) = \frac{\frac{1}{N}\sum_{k=1}^{N} \delta T_{QT}^{k+j-1} \delta T_{RR}^k}{\sigma_{QT}\sigma_{RR}}, \quad j = 1, 2, \ldots, M (M \leq N), \quad (S.6)$$

where N is the number of samples. When j=1, the cross-correlation coefficient coincides with the correlation coefficient given by Eq.(S.4), $$k_{RR}^{QT}(1) = k_{QR}. \text{ At } j > 1$$

the cross-correlation coefficient reflects more long-term effects. If the long-living eigen-oscillations accompany cardiac conduction, this coefficient will be reduced so its values at j>1 reflect their long-term blurring effect. Without loss of generality we shall discuss below the case with M=N. The discrete Fourier transform (DFT) of $$k_{RR}^{QT}(j)$$

is then within a factor equal to the product of normalized DFT amplitudes, $[\delta \tilde{T}_{RR}(\omega_m)/\sigma_{RR}][\delta \tilde{T}_{QT}(\omega_m)/\sigma_{QT}]$, corresponding to the normalized fluctuations $\delta T_{RR}^k/\sigma_{RR}$ and $\delta T_{QT}^k/\sigma_{QT}$, respectively (where a tilde indicates DFT, $\omega_m = m\omega_0$, m=1, 2, ..., N, and $\omega_0 = 2\pi/(N\tau)$ with $\tau$ being a sampling period,). Similarly to the Wiener-Khinchin theorem the sum $$\sum_j |k_{RR}^{QT}(j)|^2$$

can be proven to be equal (within a constant factor) to $$\sum_m |\delta \tilde{T}_{RR}(\omega_m) \delta \tilde{T}_{QT}(\omega_m)|^2.$$

This suggests an alternative way to measure the degree of causal dependence between QT and RR intervals by the overlap integral of the spectral densities of the QT and RR fluctuations, which has the form $$K_{QR} = \sum_{m=1}^{N} \frac{|\delta \tilde{T}_{RR}(\omega_m) \delta \tilde{T}_{QT}(\omega_m)|^2}{(\sigma_{RR}\sigma_{QT})^2} \quad (S.7)$$

Notice that expression (S.7) can generally be evaluated without beat-to-beat recordings. This dimensionless quantity reflects all subsequent functional QT responses on a variation of a cardiac cycle length. In the presence of long-living eigen-oscillations of the excitation wave properties such functional responses must be completely smeared so that $K_{QR}$ has to be relatively small. Therefore, a small value of $K_{QR}$ may also reflect the presence of long-living eigen-oscillations and indicate a conduction instability. Thus, as the quantity $K_{QR}$ can be taken as an independent partial measure of the arrhythmia risk. The corresponding partial stability criterion has the form $$K_{QR} > K_{crit} \quad (S.8)$$

The aggregated stability measure and criterion. The above three stability measures can be aggregated into one stability measure C as follows $$C = \frac{F_1(s)}{F_2(k_{QR})F_3(K_{QR})} \quad (S.9)$$

where $F_1(.)$, $F_2(.)$, and $F_3(.)$ are monotonically growing functions, representing nonlinear scaling transformations of the corresponding partial stability measures. If all three partial instability conditions (S.3), (S.5) and (S.8) are satisfied, we have $$C > C_{crit} \equiv \frac{F_1(s_{crit})}{F_2(\kappa_{crit})F_3(K_{crit})} \quad (S.10)$$

In this case all three partial criteria indicate an elevated risk to develop an arrhythmia, which is reflected in an elevated value of the agglomerated stability measure, C, that exceeds $C_{crit}$. In general, there are logical reasons to expect that the larger the value of the aggregated quantity C in a given subject the higher the risk of the occurrence of an arrhythmia in this subject during a given time period in the future. Therefore, the quantity C can serve as an aggregated arrhythmia risk measure, and can be used within an aggregated arrhythmia risk criterion of the form (S.10) with an empirically established critical value of $C_{crit}$.

4. Fluctuation Analysis Methods for the Assessment of the Stability Measures

Stability measures $k_{QR}$ and $K_{QR}$ and, as it will be shown below, s, are expressed via QT and RR fluctuation time series. These fluctuations thus must be extracted from the original data sets.

An algorithm for finding and separating the trend and fluctuations. A theoretical basis for the following data processing concerning the case with non-stationary mean value and stationary increments (first differences) has been first laid by A. Kolmogoroff (Soviet Mathematics, Doklady, 26:6–9 (1940); and 26:115–118(1940)) and later developed by Yaglom (Matematicheskii Sbornik, 37:141–196(1955)) for the case with stationary higher order differences. Let us denote for brevity the QT or RR interval immediately preceding a time instant t by a single quantity, T(t). Measurements of T(t) result in a discrete time series, which is a sample of the stochastic process T(t), which can be divided into two components, a nonrandom component $f(t)$ and a random component (fluctuations or physiological and physical noise) $\phi(t)$, so we have $$T(t) = \overline{T}(t) + \delta T(t), \overline{T}(t) \equiv <T>, <\delta T(t)> = 0, \quad (F.1)$$

where the angle brackets denote ensemble averaging. The condition that the ensemble average of the fluctuations $<\delta T>$ is zero is of crucial importance and must be preserved by any consistent data processing procedure. We shall consider sufficiently short segments of data records such that the random component, $\delta T(t)$, can be considered as a stationary stochastic process with zero mean, and time independent moments. We denote for brevity by $\{T^k\}$ (k=1, 2, ..., N), either $\{T^k_{RR}\}$ or $\{T^k_{QT}\}$. Let us consider a short segment of data $\{T^k\}$ such that the trend can be accurately represented by a low power polynomial, e.g., a linear, or quadratic, in the vicinity of the minimum. In the former case we represent the sequence $T^k$ on the segment by the expression $$T^k = b(t_k - t_1) + c + \delta T^k, \quad (F.2)$$

where $\delta T^k$ by definition is the k-th fluctuation if b and c are determined by the requirement that the error E is minimized:

$$E \equiv \sum_{k=1}^{N} (\delta T^k)^2 = \min_{b,c} \quad (F.3)$$

This condition determines the coefficients a and b and thereby a sequence of the varying trend values, $\overline{T}(t_k) = b(t_k - t_1) + c$, and the fluctuation time series, $\delta T(t_k) \equiv \delta T^k$ for k=1, ,2 ..., N. In the vicinity of the HR maximum, or RR (QT) interval minimum, one needs to use a parabolic fit for the trend and set $$T^k = a(t_k - t_1)^2 + b(t_k - t_1) + c + \delta T^k \quad (F.4)$$

and determine the coefficients a, b and c by the requirement $$E \equiv \sum_{k=1}^{N} (\delta T^k)^2 = \min_{a,b,c} \quad (F.5)$$

One can easily check that one of the minimization equations, $\partial E/\partial c = 0$, reduces to the requirement that $$\sum_{k=1}^{N} \delta T^k = 0, \quad (F.6)$$

which, indeed, allows one to interpret the series $\{\delta T^k\}$ as a series of fluctuations, a stationary random process with a zero mean value. It is also noteworthy that under the condition of quasi-stationarity the above constants a and b are sufficiently small so the trend variation of function $\overline{T}(t)$ is much smaller than its representative value on the segment. In the linear case it means that the following condition holds $$b(t_N - t_k) < b(t_N - t_1) << c, (k=1,2, ..., N). \quad (F.7)$$

Similarly, in the quadratic case it means that $$a(t_N - t_k)^2 < a(t_N - t_1)^2 << c, b(t_N - t_1) << c, (k=1,2, ..., N). \quad (F.8)$$

An assessment of the transversal slope as the ratio of standard deviations of QT and RR intervals. A random element for ventricular conduction is the randomness of the pacing signal from the cardiac pacemaker (sino-atrial node). This means that an instant at which a wave is initiated is somewhat random, although its mean value in a steady sate is constant and is well characterized by the instantaneous value of the mean rate. Considering an arbitrary cardiac cycle and omitting for brevity the corresponding superscript we can be present it in the form $$T_{RR} = <T_{RR}> + \delta T_{RR} \tag{F.9}$$

where the angular brackets denote averaging so that $<T_{RR}>$ is the current mean value of the RR-interval and $\delta T_{RR}$ is the random RR-interval fluctuation with zero mean value. We thus by definition have $$<\delta T_{RR}> = 0. \tag{F.10}$$

Similarly one can introduce fluctuations $\delta T_{QT}$ of the QT-interval $T_{QT}$ and write $$T_{QT} = <T_{QT}> + \delta T_{QT} \tag{F.11}$$

where $<T_{QT}>$ is the current mean value of the QT-interval and $\delta T_{QT}$ is the random fluctuation with zero mean value:

$$<\delta T_{QT}> = 0. \tag{F.12}$$

During stationary propagation the duration of the QT-interval, $T_{QT}$ for each beat is related to the value of $T_{RR}$ (at the previous beat) by the restitution relation $T_{QT}^{n+1} = r(T_{RR}, T_{RR}^{n+1})$, and, since the value of $T_{RR}$ fluctuates, the value of $T_{QT}$ must fluctuate accordingly. Substituting Eq-s (F.9) and (F.11) into the restitution relation and omitting the subscripts for brevity, we have $$<T_{QT}> + \delta T_{QT} = r(<T_{RR}>, <T_{RR}> + \delta T_{RR}) \tag{F.13}$$

Expanding the function r in the Taylor series, we obtain within the second order $$<T_{QT}> + \delta T_{QT} \approx r(<T_{RR}>, <T_{RR}>) + r_t'(<T_{RR}>, <T_{RR}>) \delta T_{RR} + \frac{1}{2} r_{tt}''(<T_{RR}>, <T_{RR}>)(\delta T_{RR})^2 \tag{F.14}$$

where subscript, t, indicates that the partial derivative is taken with respect to the second, test, variable. Taking square of both sides and neglecting all terms higher than the second order yields $$<T_{Qt}>^2 + 2<T_{QT}> \delta T_{Qt} + (\delta T_{QT})^2 \approx r^2 + 2rr_t' \delta T_{RR} + [rr_{tt}'' + (r_t')^2](\delta T_{RR})^2 \tag{F.15}$$

Averaging Eq-s (F.14) and (F.15) and using zero-sum conditions (F.10) and (F.12), we respectively have $$<T_{QT}> = r(<T_{RR}>, <T_{RR}>) + \frac{1}{2} r_{tt}''(<T_{RR}>, <T_{RR}>) < (\delta T_{RR})^2 > \tag{F.16}$$

and $$<T_{QT}>^2 + <(\delta T_{QT})^2> = r^2 + 2[rr_{tt}'' + (r_t')^2]<(\delta T_{RR})^2> \tag{F.17}$$

Now substituting Eq.(F.16) into (F.17), neglecting the 4th order term and simplifying, we obtain $$<(\delta T_{QT})^2> = (r_t')^2 <(\delta T_{RR})^2> \tag{F.18}$$

This expression allows one to find the explicit expression for the slope in the form $$s \equiv r_t'(\overline{T}_{RR}, \overline{T}_{RR}) = \sqrt{\frac{<(\delta T_{QT})^2>}{<(\delta T_{RR})^2>}} \equiv \frac{\sigma_{QT}}{\sigma_{RR}} \tag{F.19}$$

where $\sigma_{QT}$ and $\sigma_{RR}$ are the corresponding standard deviations. The quantity $\overline{T}_{RR}$ is the time-average RR interval, which coincides with the ensemble average $<T_{RR}>$ under the condition of stationarity or quasi-stationarity. Both numerator and denominator in the right hand side of Eq.(27) can be measured directly and independently. Thus, Eq.(27) allows us to directly assess the slope of the restitution curve $r(\overline{T}_{RR}, \overline{T}_{RR})$ at both the training and the testing cardiac cycle length equal to the same value of $\overline{T}_{RR}$, which is assumed to be constant on the average. Such a stationarity condition is nonrestrictive for long-term ECG recordings obtained via a Holter monitor or a similar device. On the other hand if the systematic change in the mean heart rate occurs very slowly, as under our quasi-stationary exercise protocol, then during reasonably short time segments the change in the heart rate can safely be neglected. For example, under one version of our exercise protocol the typical change in the heart rate is about 4 beat/min. Therefore, if we choose data collection time segments of 15 seconds, the systematic change in the mean heart rate will not exceed 1 beat/min, which is of the order of one percent and is negligible, indeed.

Having found the fluctuations for RR and QT intervals within a time window, one can immediately evaluate the slope of the restitution curve. Let us denote the RR and QT fluctuation time series, respectively, by $\{\delta T^k_{RR}\}$ $\{\delta T^k_{QT}\}$ (k=1, 2, ..., N). The corresponding standard deviations are evaluated as $$\sigma_{RR} = \sqrt{\frac{1}{N-1} \sum_{k=1}^{N} (\delta T^k_{RR})^2}, \; \sigma_{QT} = \sqrt{\frac{1}{N-1} \sum_{k=1}^{N} (\delta T^k_{QT})^2} \tag{F.20}$$

The transversal slope, s, is then assessed as $$s = \frac{\sigma_{QT}}{\sigma_{RR}} \tag{F.21}$$

According to this equation the slope in question is equal to the ratio of the instantaneous standard deviations of the QT and RR intervals. The proposed method consists of (a) measuring a set of RR and QT intervals for an appropriate sample of cardiac cycles within a short time window, (b) proper data processing, a regression analysis with which the trends, the dependences of the mean RR and QT interval values on time within the time window, are evaluated, (c) separating the trend from fluctuations and obtaining a sample of fluctuations of RR and QT intervals, each with zero mean value (d) calculating the standard deviation averaging the fluctuations and then (e) finding their ratio that provides an estimate of the slope in question. This method is robust, easy to implement, and generally does not require beat-to-beat sampling. Its precision is higher when the QT and RR interval fluctuations are sufficiently small. This condition is well satisfied under our quasi-stationary exercise protocol. An alternative case with large fluctuations typical for regular Holter recordings can be treated similarly using higher power expansions in Eq. (F.14).

5. Testing Methods

The methods of the present invention are primarily intended for the testing of human subjects. Virtually any human subject can be tested by the methods of the present invention, including male, female, juvenile, infant, adolescent, adult, and geriatric subjects. The methods may be carried out as an initial screening test on subjects for whom no substantial previous history or record is available, or may be carried out on a repeated basis on the same subject (particularly where a comparative quantitative indicium of an individual's cardiac health over time is desired) to assess the effect or influence of intervening events and/or intervening therapy on that subject between testing sessions.

As noted above, the method of the present invention generally comprises (a) collecting at least one QT and RR interval data set from the subject during (i) a stage of gradually increasing heart rate, (ii) a stage of gradually decreasing heart rate, or (iii) both a stage of gradually increasing heart rate and gradually decreasing heart rate; (b) separating fluctuations from slow trends in said at least one QT and RR interval data set; (c) comparing said QT and RR fluctuations to one another to determine the difference therebetween; and (d) generating from the comparison of step (c) a measure of risk of cardiac arrhythmia in said subject. A greater difference between QT and RR fluctuations indicates greater risk of cardiac arrhythmia in said subject.

The stages of gradually increasing and/or gradually decreasing heart rate are carried out during a gradual exercise protocol in a manner that maintains during these periods essentially or substantially the same stimulation of the heart by the peripheral nervous and hormonal control systems. These stages can be also found and selected from arbitrary continuous Holter monitoring records. This methodology can be carried out by a variety of techniques, with the technique of conducting or selecting one and/or several consecutive or isolated stages of gradually increasing and gradually decreasing average heart rates.

The stage of gradually increased average heart rate and the stage of gradually decreased average heart rate may be the same in duration or may be different in duration. In general, each stage is at least 3, 5, 8, or 10 minutes or more in duration. Together, the duration of the two stages may be from about 6, 10, 16 or 20 minutes in duration to about 30, 40, or 60 minutes in duration or more. The two stages are preferably carried out sequentially in time—that is, with one stage following after the other substantially immediately, without an intervening rest stage. In the alternative, the two stages may be carried out separately in time, with an intervening "plateau" stage (e.g., of from 1 to 5 minutes) during which cardiac stimulation or exercise load is held substantially constant, before the stage of decreasing load is initiated. One and/or several gradual slow trend stages can be selected from the continuous Holter recording in the same mainer.

The exercise protocol may include the same or different sets of load steps during the stages of increasing or decreasing heart rates. For example, the peak load in each stage may be the same or different, and the minimum load in each stage may be the same or different. In general, each stage consists of at least two or three different load levels, in ascending or descending order depending upon the stage. Relatively high load levels, which result in relatively high heart rates, can be used but are not essential. An advantage of the present invention is that its sensitivity allows both exercise procedures to be carried out at relatively low load levels that do not unduly increase the pulse rate of the subject. For example, the method may be carried out so that the heart rate of the subject during either the ascending or descending stage (or both) does not exceed about 140, 120, or even 100 beats per minute, depending upon the condition of the subject. Of course, data collected at heart rates above 100, 120, or 140 beats per minute may also be utilized if desired, again depending upon the condition of the subject.

For example, for an athletic or trained subject, for the first or ascending stage, a first load level may be selected to require a power output of 60 to 100 or 150 watts by the subject; an intermediate load level may be selected to require a power output of 100 to 150 or 200 watts by the subject; and a third load level may be selected to require a power output of 200 to 300 or 450 watts or more by the subject. For the second or descending stage, a first load level may be selected to require a power output of 200 to 300 or 450 watts or more by the subject; an intermediate or second load level may be selected to require a power output of 100 to 150 or 200 watts by the subject; and a third load level may be selected to require a power output of 60 to 100 or 150 watts by the subject. Additional load levels may be included before, after, or between all of the foregoing load levels as desired, and adjustment between load levels can be carried out in any suitable manner, including step-wise or continuously.

In a further example, for an average subject or a subject with a history of cardiovascular disease, for the first or ascending stage, a first load level may be selected to require a power output of 40 to 75 or 100 watts by the subject; an intermediate load level may be selected to require a power output of 75 to 100 or 150 watts by the subject; and a third load level may be selected to require a power output of 125 to 200 or 300 watts or more by the subject. For the second or descending stage, a first load level may be selected to require a power output of 125 to 200 or 300 watts or more by the subject; an intermediate or second load level may be selected to require a power output of 75 to 100 or 150 watts by the subject; and a third load level may be selected to require a power output of 40 to 75 or 100 watts by the subject. As before, additional load levels may be included before, after, or between all of the foregoing load levels as desired, and adjustment between load levels can be carried out in any suitable manner, including step-wise or continuously.

The heart rate may be gradually increased and gradually decreased by subjecting the patient to a predetermined schedule of stimulation. For example, the patient may be subjected to a gradually increasing exercise load and gradually decreasing exercise load, or gradually increasing electrical or pharmacological stimulation and gradually decreasing electrical or pharmacological stimulation, according to a predetermined program or schedule. Such a predetermined schedule is without feedback of actual heart rate from the patient. In the alternative, the heart rate of the patient may be gradually increased and gradually decreased in response to actual heart rate data collected from concurrent monitoring of said patient. Such a system is a feedback system. For example, the heart rate of the patient may be monitored during the test and the exercise load (speed and/or incline, in the case of a treadmill) can be adjusted so that the heart rate varies in a prescribed way during both stages of the test. The monitoring and control of the load can be accomplished by a computer or other control system using a simple control program and an output panel connected to the control system and to the exercise device that generates an analog signal to the exercise device. One advantage of such a feedback system is that (if desired) the control system can insure that the heart rate increases substantially linearly during all slow trend stages.

The generating step (d) may be carried out by any suitable means, such as by generating curves from the data sets (with or without actually displaying the curves), and then (i) directly or indirectly evaluating a measure (e.g., a slope of the restitution curve), a greater measure indicating greater susceptibility to cardiac arrhythmias in said subject, (ii) directly or indirectly comparing the shapes (e.g., slopes or derivatives thereof) of the different curves, with a greater difference in shape indicating greater susceptibility to cardiac arrhythmias in the subject; or (iii) combinations of (i) and (ii). Specific examples are given in Examples 7–10 below.

The method of the invention may further comprise the steps of (e) comparing the measure of susceptibility to cardiac arrhythmias to at least one reference value (e.g., a mean, median or mode for the quantitative indicia from a population or subpopulation of individuals) and then (f) generating from the comparison of step (e) at least one quantitative indicium of cardiovascular health for said subject. Any such quantitative indicium may be generated on a one-time basis (e.g., for assessing the likelihood that the subject is at risk to experience a future arrhythmia-related cardiac incident such as ventricular tachycardia or fibrillation), or may be generated to monitor the progress of the subject over time, either in response to a particular prescribed cardiovascular therapy, or simply as an ongoing monitoring of the physical condition of the subject for improvement or decline (again, specific examples are given in Examples 7–10 below). In such a case, steps (a) through (f) above are repeated on at least one separate occasion to assess the efficacy of the cardiovascular therapy or the progress of the subject. A decrease in the difference between said data sets from before said therapy to after said therapy, or over time, indicates an improvement in cardiac health in said subject from said cardiovascular therapy. Any suitable cardiovascular therapy can be administered, including but not limited to, aerobic exercise, muscle strength building, change in diet, nutritional supplement, weight loss, smoking cessation, stress reduction, pharmaceutical treatment (including gene therapy), surgical treatment (including both open heart and closed heart procedures such as catheter ablation, pacemaker or defibrillator implantation etc.) and combinations thereof.

The therapy or therapeutic intervention may be one that is approved or one that is experimental. In the latter case, the present invention may be implemented in the context of a clinical trial of the experimental therapy, with testing being carried out before and after therapy (and/or during therapy) as an aid in determining the efficacy of the proposed therapy.

6. Testing Apparatus

Figure 3:
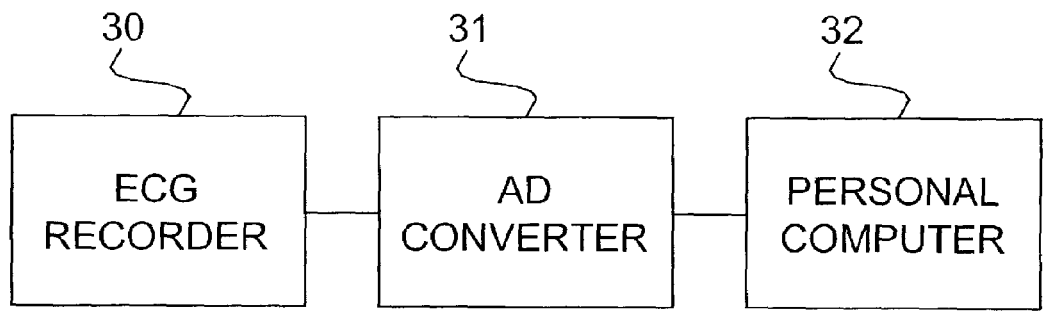
FIG. 3 is a block diagram of an apparatus for carrying out the present method.

FIG. 3 provides an example of the apparatus for data acquisition, processing and analysis by the present invention. Electrocardiograms are recorded by an ECG recorder, via electrical leads placed on a subject's body. The ECG recorder may be, for example, a standard multi-lead Holter recorder or any other appropriate recorder. The analog/digital converter digitizes the signals recorded by the ECG recorder and transfers them to a personal computer, or other computer or central processing unit, through a standard external input/output port. The digitized ECG data can then be processed by standard computer-based waveform analyzer software. Restitution curves and a cardiac or cardiovascular health indicium or other quantitative measure of the presence, absence or degree of susceptibility to cardiac arrhythmias can then be calculated automatically in the computer through a program (e.g., Basic, Fortran, C++, etc.) implemented therein as software, hardware, or both hardware and software.

Figure 4A:
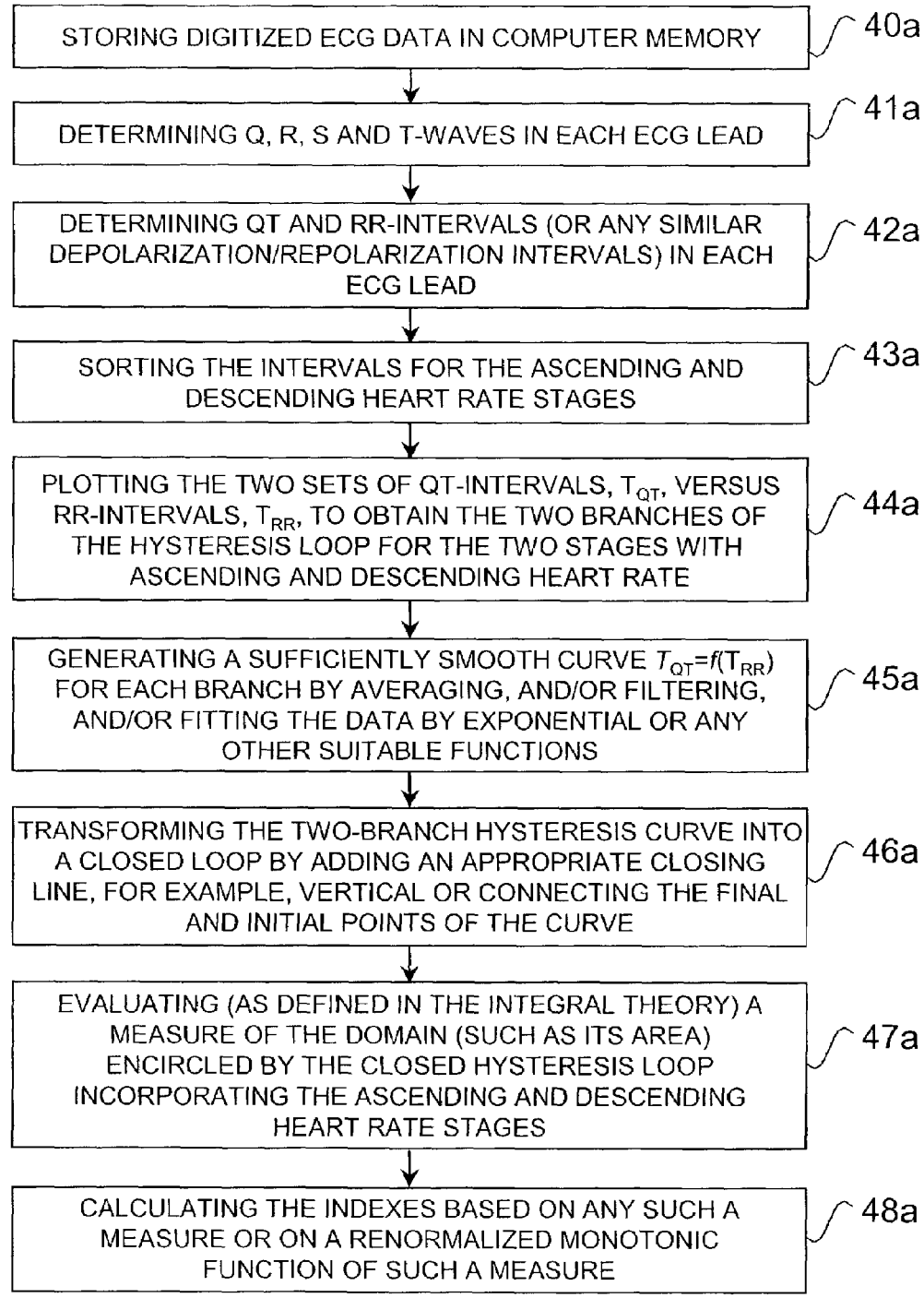
FIG. 4 is a block diagram of the processing steps for data acquisition and analysis of the present invention.
Figure 4B:
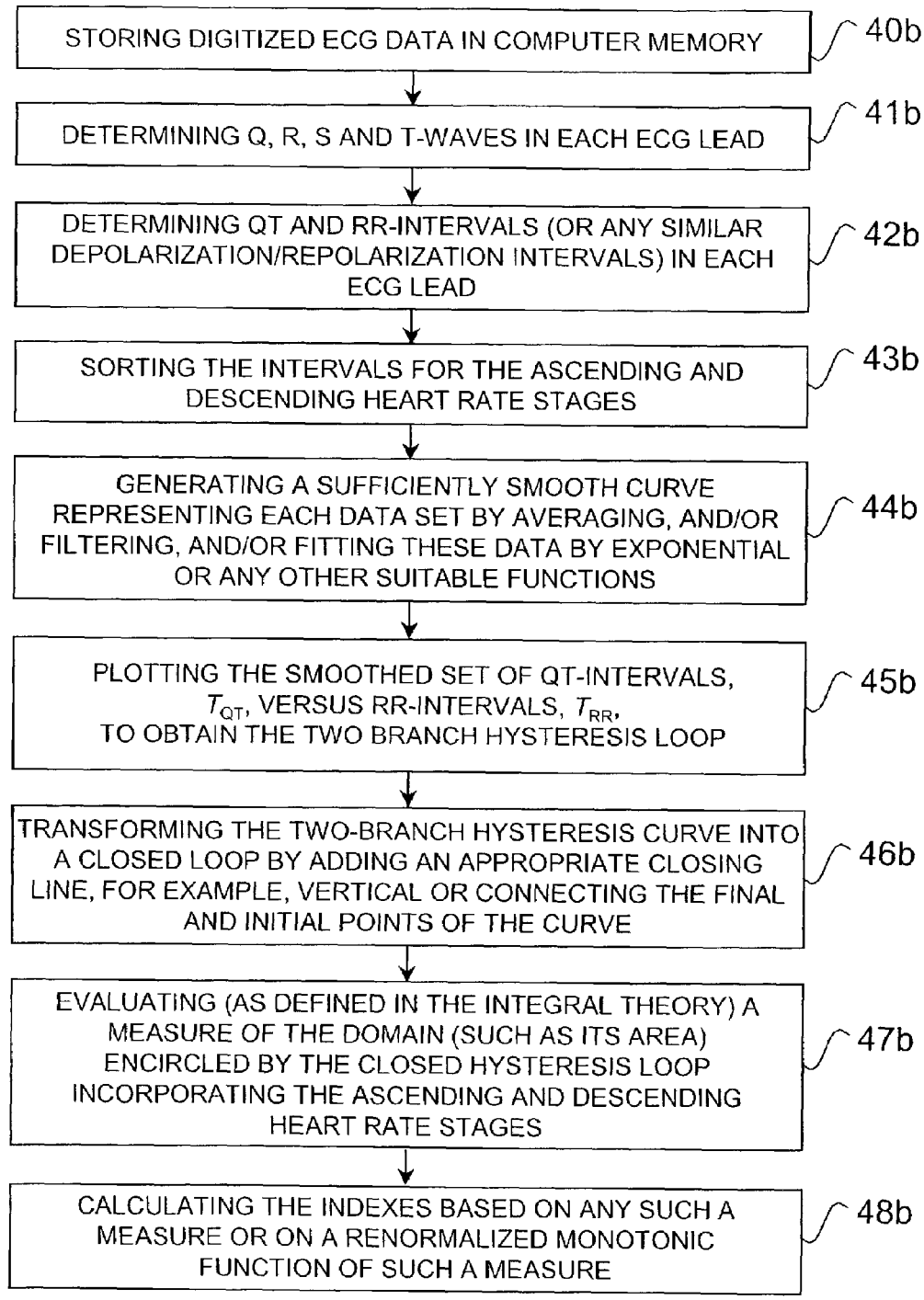

FIG. 4 illustrates the major steps of digitized data processing in order to generate an analysis of a QT-RR data set collected from a subject during quasi-stationary changes in physiological conditions. The digitized data collected from a multi-lead recorder are stored in a computer memory for each lead as a data array (4a) The size of each data array is determined by the durations of the ascending and descending heart rate stages and a sampling rate used by the waveform analyzer, which processes an incoming digitized ECG signal. The waveform analyzer software first detects major characteristic waves (Q, R, S and T waves) of the ECG signal in each particular lead (4b). Then in each ECG lead it determines the time intervals between consecutive R waves and the beginning of Q and the end of T waves (4c). Using these reference points it calculates heart rate and RR and QT intervals. Then, the application part of the software sorts the intervals for the ascending and descending heart rate stages (4d). A part of the application software performs the next step (4e), which is smoothing, filtering or data fitting, using any suitable functions, in order to obtain sufficiently smooth QT and RR slow trends for each gradual stage. At the next step (4f) another application part of the software uses this parametric representation to separate fast QT and RR fluctuations from their smooth slow trends. At the next step (4g) the application software evaluates slopes of instantaneous restitution dependences along a slow heart rate trend and determines correlation coefficients between the QT and RR interval fluctuations and their power spectra. Such a measure is the aggregated factor of stability, which may include appropriate weight functions increasing or decreasing the contribution of different portions of the instantaneous slopes or correlations between QT and RR intervals and their power spectra into said measure. The final step (4h) of the data processing for each ECG lead is that the application software calculates indexes by appropriately renormalizing the said measure or any monotonous functions of said measure. The measure itself along with the indexes may reflect both an action potential wave instability, as well as a predisposition to cardiac arrhythmias, that can be reflected in some particularities of the shape of the measured restitution curves. The results of all above-mentioned signal-processing steps may be used to quantitatively assess susceptibility to cardiac ischemia and, as a simultaneous option, cardiovascular system health of a particular individual under test.

The present invention is explained in greater detail in the non-limiting examples set forth below.

EXAMPLE 1

Testing Apparatus

A testing apparatus consistent with FIG. 3 was assembled. The electrocardiograms are recorded by an RZ153PM12 Digital ECG Holter Recorder (ROZINN ELECTRONICS, INC.; 71-22 Myrtle Av., Glendale, N.Y., USA 11385-7254), via 12 electrical leads with Lead-Lock Holter/Stress Test Electrodes LL510 (LEAD-LOK, INC.; 500 Airport Way, P.O. Box L, Sandpoint, Id., USA 83864) placed on a subject's body in accordance with the manufacturer's instructions. Digital ECG data are transferred to a personal computer (Dell Dimension XPS T500MHz/Windows 98) using a 40 MB flash card (RZFC40) with a PC 700 flash card reader, both from Rozinn Electronics, Inc. Holter for Windows (4.0.25) waveform analysis software is installed in the computer, which is used to process data by a standard computer-based waveform analyzer software. Restitution curves and an indicium that provides a quantitative characteristic of the extent of susceptibility to cardiac arrhythmias are then calculated manually or automatically in the computer through a program implemented in Fortran 90.

Experimental data were collected during an exercise protocol programmed in a Landice L7 Executive Treadmill (Landice Treadmills; 11 Canfield Av., Randolph, N.J. 07869). The programmed protocol included 20 step-wise intervals of a constant exercise load from 48 seconds to 1.5 minutes each in duration. Altogether these intervals formed two equal-in-duration gradually increasing and gradually decreasing exercise load stages, with total duration varying from 16 to 30 minutes. For each stage a treadmill belt speed and elevation varied there-and-back, depending on the subject's age and health conditions, from 1.5 miles per hour to 5.5 miles per hour and from one to ten degrees of treadmill elevation, respectively.

EXAMPLE 2

Figure 5:
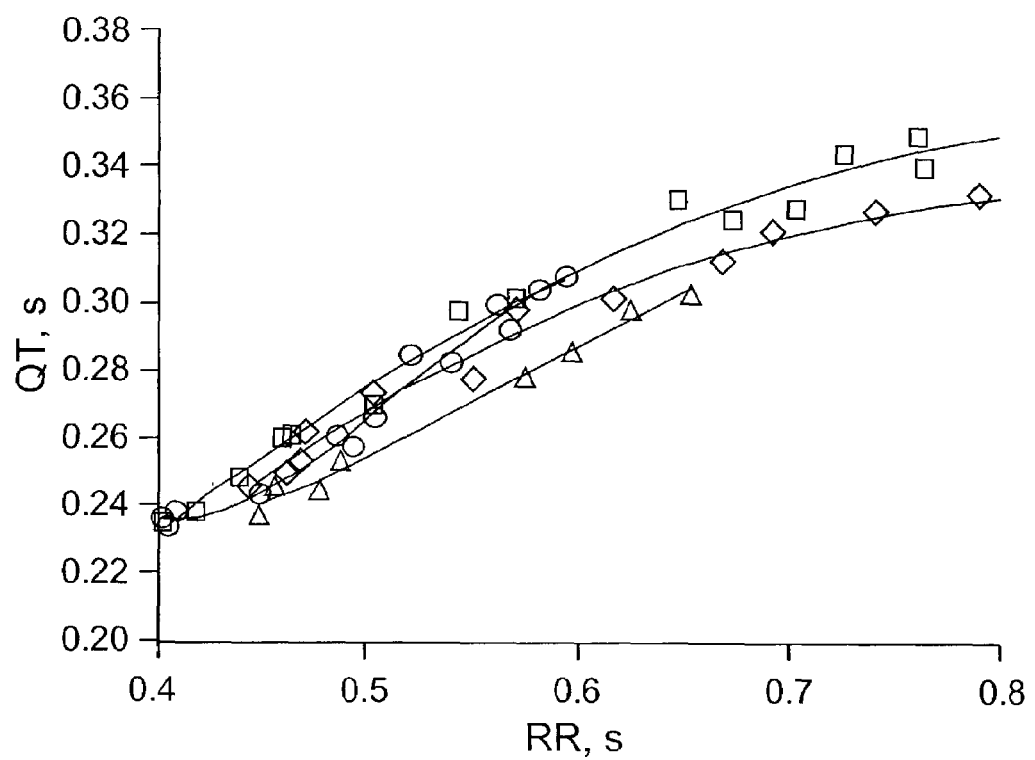
FIGS. 5–6 illustrate slopes of experimental restitution curves and power spectra of the QT and RR interval fluctuations for healthy subjects without coronary artery disease (CAD). Curves 1,2 and 3 (FIG. 5) and charts 6 (1–3) show the slopes and power spectra for 47, 50 and 58 year old male subjects, respectively. Curves 4 and 5 (FIG. 5) and charts 6 (4,5) reflect the slopes and power spectra for 57 and 58 year old female subjects, respectively. Dashed and solid curves in all fragments of the FIG. 6 correspond to the QT and RR interval fluctuations, respectively.
Figure 6:
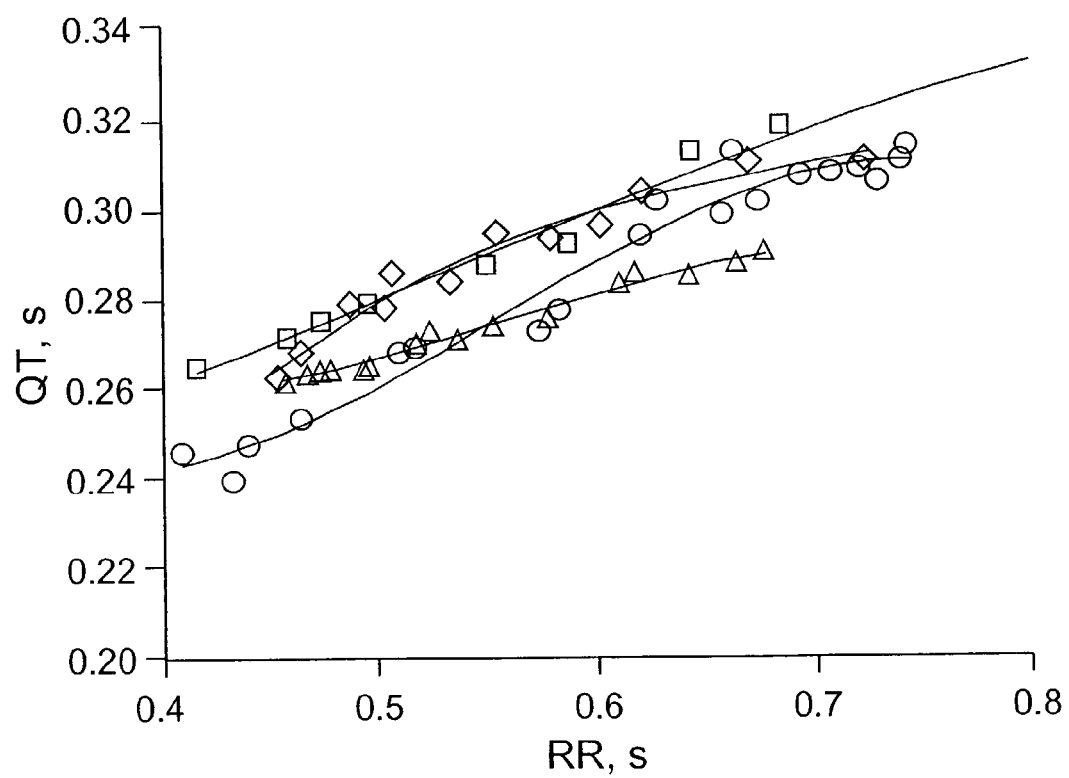

Restitution Curves' Slopes and Power Spectra of the QT and RR Interval Fluctuations in Healthy Subjects of Different Ages This example was carried out on three male and two female subjects with an apparatus and procedure as described in Example 1 above. Referring to FIGS. 5–6, one can readily see a difference in the slopes of the restitution curves and the power spectra of the QT and RR interval fluctuations of generally healthy subjects of different ages. These subjects exercised on a treadmill according to a quasi-stationary 20-minute protocol with gradually increasing and gradually decreasing exercise load. A beat sampling rate with which a waveform analyzer determines QT and RR intervals is equal to 15 samples per minute. Neither of the subjects had a conventional ischemia-induced depression of the ECG-ST segments, however one . . . year old female subject had 60 premature ventricular contractions and three very short (15–20 consecutive beats) episodes of non-sustain ventricular tachycardia (VT). The dependences shown in FIGS. 5–6, clearly demonstrate that the method of the present invention allows one to observe a difference within a conventionally sub-threshold range of susceptibility to initiation of unstable propagation and allows one to quantitatively differentiate between the reserve of stability of cardiac rhythm of all reflected subjects. The generation of the aggregated stability measure for all of the cases shown in FIGS. 5–6 is based on partial stability measures discussed above and is given in greater detail in the specification below (example 8).

EXAMPLE 3

Figure 7:
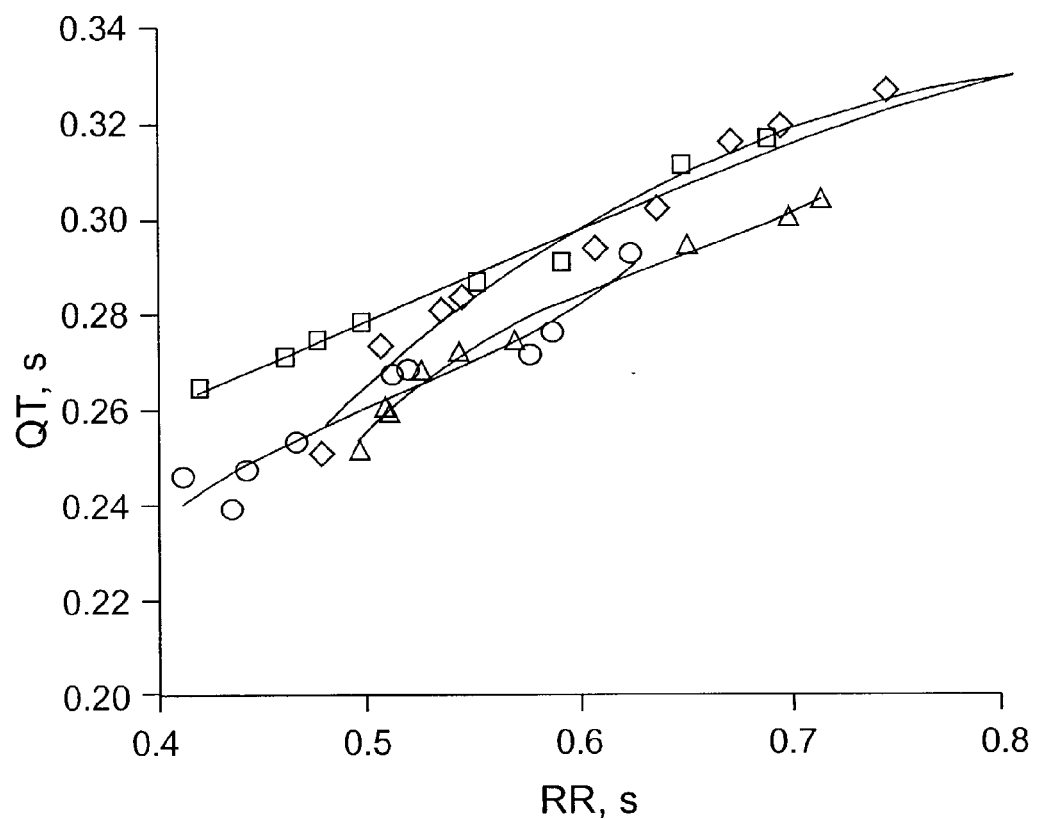
FIGS. 7–8 provide examples of the slopes of restitution curves and power spectra of the QT and RR interval fluctuations for subjects with CAD. Curves 1 and 2 (FIG. 7) and charts 8 (1,2) show the slopes and power spectra for 52-year-old female (without and with taking beta-blocker), respectively. The curve 3 and a chart 8(3) demonstrate the slopes and power spectra for 74 year old male subject. Each individual was with a prior to testing history of coronary artery disease. Dashed and solid curves in all fragments of the FIG. 8 correspond to the QT and RR interval fluctuations, respectively. The generation of the slopes of the restitution curves and the QT and RR interval fluctuations spectra is explained in greater detail in the specification below.
Figure 8:
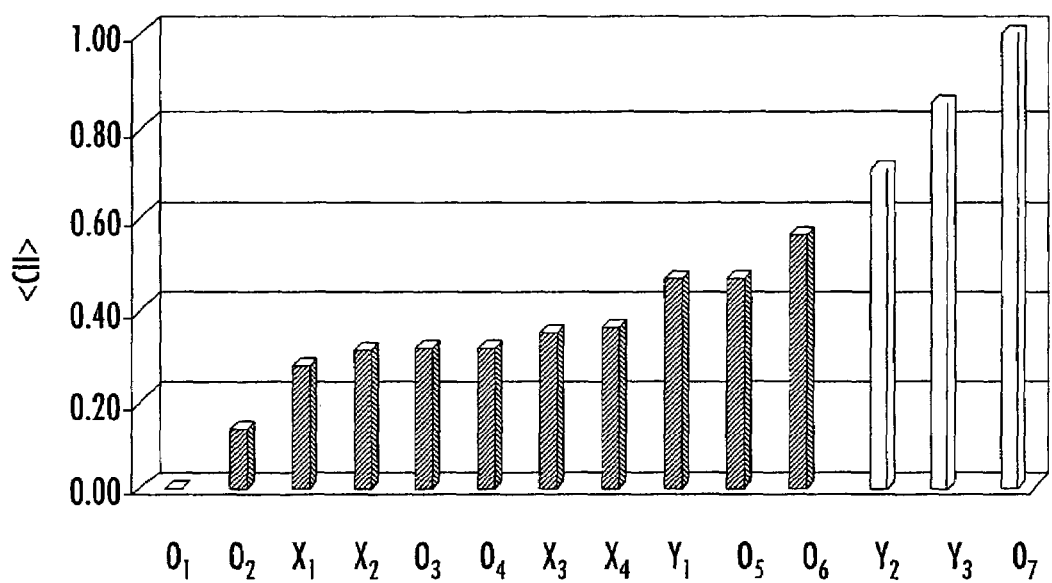

Restitution Curves' Slopes and Power Spectra of the QT and RR Interval Fluctuations for Subjects with a History of Coronary Artery Disease These examples were carried out on 52-year-old female and 74-year-old male subjects with an apparatus and procedure as described in Example I above. Both subjects had a prior history of coronary artery disease. These subjects exercised on a treadmill according to a quasi-stationary 20-minute protocol with a gradually increasing and gradually decreasing exercise load. FIGS. 7 (curves 1,2) and 8 (1,2) illustrate the slopes and power spectra of the QT and RR interval fluctuations for the female subject when she exercised without and with taking beta-blocker medication, respectively. She had a relatively high number of premature ventricular contractions, 184 (FIG. 7, curve 2 and FIG. 8(2)), during exercise, revealing almost no reserve of stability of cardiac rhythm. The slopes were higher than a threshold value 0.5 during almost a whole interval of the developed exercise load. FIG. 7 (curve 3) and 8(3) show the slopes and power spectra of the QT and RR interval fluctuations for the male subject who experienced a short (15 consecutive beats) episode of non-sustain ventricular tachycardia. In this case the slopes were higher than a 0.5 stability threshold for both developed and initial stages of exercise and the correlation between the QT and RR interval fluctuations power spectra was significantly lower than the level that reflects a typical stable functional dependence. These examples demonstrate that the method of the present invention allows one to resolve and quantitatively characterize the difference between levels of reserve and lack of stability for different clinical arrhythmias varied from benign premature ventricular contraction cases to a malignant VT. The generation of the aggregated stability measure for all of the cases shown in FIGS. 7,8 is based on partial stability measures discussed above and is given in greater detail in the specification below (example 8).

EXAMPLE 4

Illustration of Rapid Sympatho-Adrenal Transients

Figure 9:
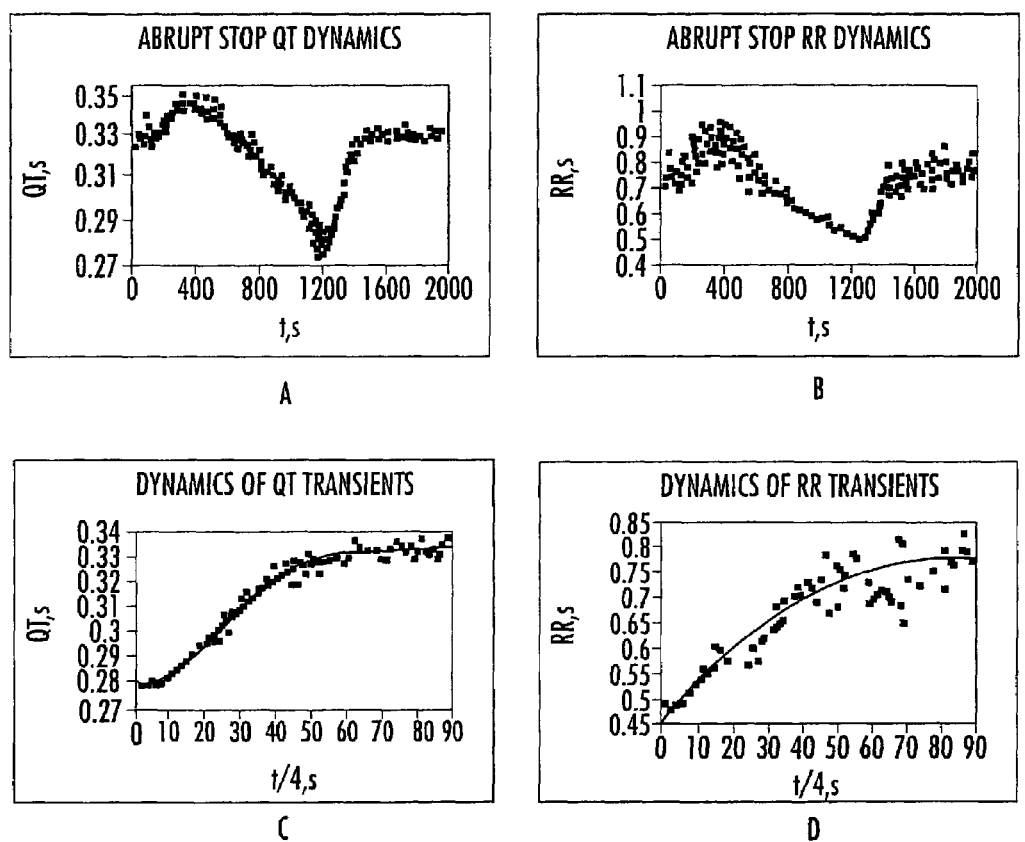
FIG. 9 illustrates a typical rapid peripheral nervous system and hormonal control adjustment of the QT and RR interval to an abrupt stop in exercise (that is, an abrupt initiation of a rest stage). This illustrates a non-quasi-stationary abrupt change, in contrast to a quasi-stationary abrupt change, as explained in greater detail below.

FIG. 9 illustrates a typical rapid sympathetic/parasympathetic nervous and hormonal adjustment of the QT (panels A, C) and RR (panels B,D) intervals to an abrupt stop after 10 minutes of exercise with increasing exercise load. All panels depict temporal variations of QT/RR intervals obtained from the right precordial lead V3 of the 12-lead multi-lead electrocardiogram. A sampling rate with which a waveform analyzer determined QT and RR intervals was equal to 15 samples per minute. A human subject (a 47 year-old male) was at rest the first 10 minutes and then began to exercise with gradually (during 10 minutes) increasing exercise load (Panels A, B-to the left from the RR, QT minima). Then at the peak of the exercise load (heart rate about 120 beat/min) the subject stepped off the treadmill in order to initialize the fastest RR and QT interval's adaptation to a complete abrupt stop of the exercise load. He rested long enough (13 minutes) in order to insure that QT and RR intervals reached post-exercise average stationary values. Panels C and D demonstrate that the fastest rate of change of QT and RR intervals occurred immediately after the abrupt stop of the exercise load. These rates are about 0.015 s/min for QT intervals while they vary from 0.28 s to 0.295 s and about 0.15 s/min for RR intervals while they grow from 0.45 s to 0.6 s. Based on the above-described experiment, a definition for "rapid sympatho-adrenal and hormonal transients" or "rapid autonomic nervous system and hormonal transients" may be given.

Rapid transients due to autonomic nervous system and hormonal control refer to the transients with the rate of 0.15 s/min for RR intervals, which corresponds to the heart rate's rate of change of about 25 beats/min, and 0.02 s/min for QT intervals or faster rates of change in RR and QT intervals in response to a significant abrupt change (stop or increase) in exercise load (or other cardiac stimulus). The significant abrupt changes in exercise load are defined here as the load variations, which cause rapid variations in QT and RR intervals, comparable in size with the entire range from the exercise peak to the stationary average rest values.

EXAMPLE 5

Illustration of a Quasi-Stationary Exercise Protocol and Slow Heart Rate Trends

Figure 10:
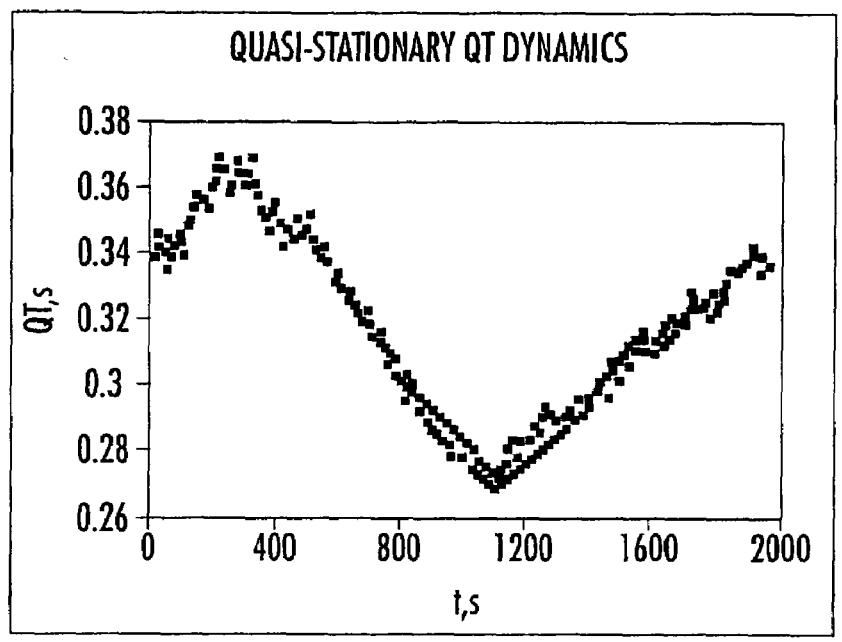
FIG. 10 illustrates a typical slow trend (quasi-stationary) QT and RR interval adjustment measured during gradually increasing and gradually decreasing cardiac stimulation.
Figure 10:
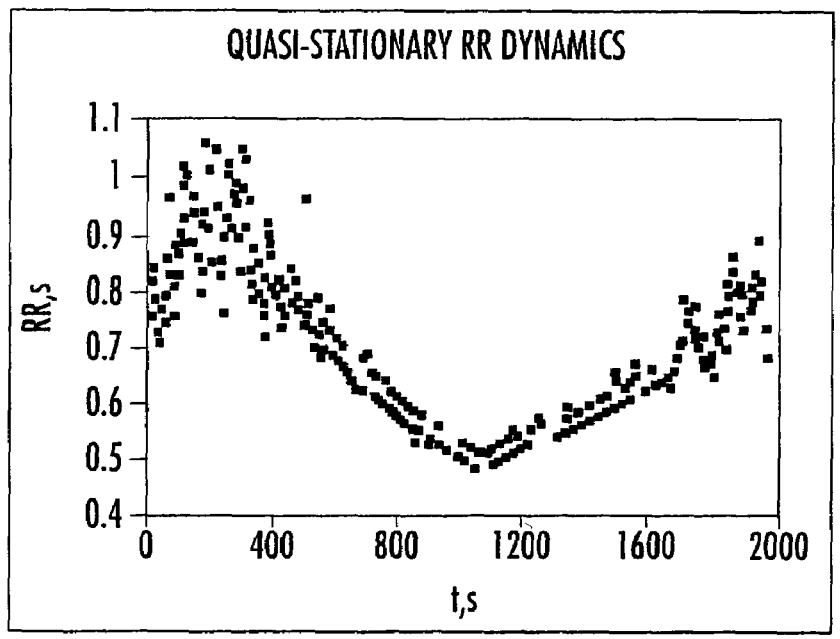

FIG. 10 illustrates a typical slow (quasi-stationary) QT (panel A) and RR (panel B) interval adjustment measured during gradually increasing and gradually decreasing exercise load in a right pre-cordial V3 lead of the 12 lead electrocardiogram recording. The sampling was 15 QT and RR intervals per minute. A male subject exercised during two consecutive 10 minute long stages of gradually increasing and gradually decreasing exercise load. Both QT and RR intervals gradually approached the minimal values at about a peak exercise load (peak heart rate ~120 beat/min) and then gradually returned to levels that were slightly lower than their initial pre-exercise rest values. The evolution of QT and RR intervals was well approximated by exponential fitting curves shown in ray in panels A and B. The ranges for the QT-RR interval, there-and-back, time variations were 0.34 s–0.27 s–0.33 s (an average rate of change ~0.005 s/min) and 0.79 s–0.47 s–0.67 s (an average rate of change ~0.032 s/min or 6 beat/min) for QT and RR intervals, respectively. The standard root-mean-square deviation, c, of the observed QT and RR intervals, shown by black dots in both panels, from their exponential fits were on an order of magnitude smaller than the average difference between the corresponding peak and rest values during the entire test. These deviations were $\sigma$~0.003 s for QT and $\sigma$~0.03 s for RR intervals, respectively. According to FIG. 9 (panels C, D) such small fluctuations, when associated with abrupt heart rate changes due to physiological variations or due to discontinuity in an exercise load, may develop and decay faster than in 10s, the time that is 60 times shorter than the duration of one gradual (ascending or descending) stage of the exercise protocol. Such a significant difference between the amplitudes and time constants of the QT-RR interval slow trend changes and abrupt heart rate fluctuations allows one to average these fluctuations over time and fit the QT-RR protocol duration dynamics by an appropriate smooth exponential-like function with a high order of accuracy. A simultaneous fitting procedure (panels A, B) determines an algorithm of a parametrical time dependence elimination from both measured QT-RR data sets and allows one to consider QT interval for each exercise stage as a monotonic function.

Based on the above-described experiment a definition for a gradual (slow trend), or "quasi-stationary" exercise (or stimulation) protocol, can be quantitatively specified: A quasi-stationary exercise (or stimulation) protocol refers to two contiguous stages (each stage 3, 5, 8 or 10 minutes or longer in duration) of gradually increasing and gradually decreasing exercise loads or stimulation, such as:

1. Each stage's duration is approximately an order of magnitude (e.g., at least about two, three, four, five or ten times) longer than the average duration (~1 minute) of a heart rate adjustment during an abrupt stop of the exercise between average peak load rate (~120–150 or 160 beat/min) and average rest (~50–70 or 80 beat/min) heart rate values.

2. The standard root-mean-square deviations of the original QT/RR interval data set from their smooth and monotonic (for each stage) fits are of an order of magnitude (e.g., at least about two, three, four, five or ten times) smaller than the average differences between peak and rest QT/RR interval values measured during the entire exercise under the quasi-stationary protocol.

As shown above (FIG. 10) a gradual quasi-stationary protocol itself, which results in slow trend heart changes, allows one to separate fast time dependent fluctuations from measured QT-RR interval data sets because these fluctuations have short durations and small amplitudes. Specific algorithms of that kind of separation and generating a quantitative measure of susceptibility to unstable cardiac rhythms will be described below in example 6.

EXAMPLE 6

Fluctuation Analysis Method for the Assessment of the Stability of Excitation Wave Propagation in Cardiac Muscle and Likelihood of Cardiac Arrhythmias An example of the algorithm: local fit approach. Let $\{(t_k, T_k): k=1,2, \ldots N\}$ be a set of data points (times are equidistant, $t_k - t_{k-1} =$ const) that gives rise to a curve obtained in the quasi-stationary exercise test (FIG. 10). Similar data processing can be performed for the data set obtained from a regular Holter recording. The set $\{T_k\}$ may represent either RR-intervals, $\{T^k_{RR}\}$ or QT-intervals, $\{T^k_{QT}\}$. We define a k-th time window as a set of s+r+1 points $\{\{(t_j, T_j): j=k-s, k-s+1, \ldots k+r\}\}$ that include and surround point $(t_k, T_k)$. Let us denote by $f_k(t)$ a quadratic or linear polynomial obtained by a linear regression such that $(t, f_k(t))$ provides best fit for the data points $(t_j, T_j)$ within the window. We then choose an integer number m, ($m \leq r+s+1$) and define the standard deviation by the equation $$\sigma_k^m = \sqrt{\frac{1}{2m} \sum_{j=k-m}^{j=k+m} [T_j - f_k(t_j)]^2} \qquad (14)$$

The value of m is chosen slightly different than half width of the time window to ensure good fit for k near the end and extremum points of the data set. Having evaluated the standard deviation for QT and RR intervals within the same, k-th, time window via equation (14) we then evaluate the slope $R'(t_k)$ as their ratio via Eq. (13). If N is the total size of the sample (number of data points) this procedure must be performed N–2m times. All assessed $r'_t$ values are then compared with $s_{crit}$ in order to assess the risk of the development of cardiac arrhythmia.

EXAMPLE 7

Aggregated Stability Measure

In this example we specify the functions $F_1(.)$, $F_2(.)$ and $F_3(.)$ in Eq. (S.8) that defines the aggregated stability measure. We shall set $$F_1(s) = \frac{s^\alpha}{\left(1 + \frac{s^\mu}{\sigma^\mu}\right)^{\alpha/\mu}}, \qquad (7.1)$$

where $\alpha$ is a non-negative constant and $\sigma$ and $\mu$ are positive constants. When $\sigma = \infty$ the function $F_1$ reduces to a power function $s^\alpha$. The constant $\sigma$ plays the role of a threshold separating the regions of strong and weak effect of the value of s on the aggregated arrhythmia risk measure. The power μ determines the width of the transitional zone between these two regions. The function $F_2(.)$ is defined as $$F_2(k_{QR}) = \frac{k_{QR}^\beta}{(\kappa^\nu + k_{QR}^\nu)^{\beta/\nu}} \quad (7.2)$$

where κ and ν are positive constants and β is a non-negative constant. The constant κ has the meaning of a threshold above which the correlation coefficient value plays a lesser role in the aggregated stability measure. One can chose, for example, $\kappa = \kappa_{crit}$. The constant ν determines the width of the transition zone between the two regions of higher and lower contribution of the correlation coefficient.

The function $F_3(.)$ can be defined in a similar way $$F_3(K_{QR}) = \frac{K_{QR}^\gamma}{(K^\rho + K_{QR}^\rho)^{\gamma/\rho}}, \quad (7.3)$$

where K and ρ are positive constants and is a non-negative constant with the meanings similar to those of θ, ν, and β. Thus, the aggregated arrhythmia risk measure can be presented in the form:

$$C = \frac{s^\alpha k_{QR}^{-\beta} K_{QR}^{-\gamma}}{[1 + (s/\sigma)^\mu]^{\alpha/\mu} (\kappa^\nu + k_{QR}^k)^{-\beta/\nu} (K^\rho + K_{QR}^\rho)^{-\gamma/\rho}} \quad (7.4)$$

When the data are not fully available one can set in Eq.(7.4) some of the α, β, γ values equal to zero.

EXAMPLE 8

Calculations of the Aggregated Stability Measure for Individual Cases Described in the Examples 2,3

The aggregated stability measure C (arrhythmia index) (7.4) was calculated for all eight cases described above in the examples 2,3. A beat sampling rate with which a waveform analyzer determined QT and RR intervals was equal to 15 samples per minute for all cases. Therefore, we set γ=0 in order to have $F_2(k_{QR})=1$ valid and to exclude unavailable beat-to-beat QT and RR interval correlation factor from the aggregated stability measure. We also set α=2, σ=∞ and γ=1, ρ=0.5, K=0 in all eight analyzed cases in order to simplify the design of the aggregated measure and simultaneously achieve the most accurate reflection of pro-arrhythmic manifestations, ranging their severity by the number of observed ventricular premature contractions (PVC) and non-sustain VT episodes. Thus, the aggregated measure of stability C was given by $$C = \frac{s^2}{\sqrt{K_{QR}}} \quad (8.1)$$

where s is the maximum slope. The value of C (arrhythmia index) are summarized in the table, which is given below:

TABLE

| Subjects | CAD | Number of PVC | Number of non-sustain VT episodes | S² | $\sqrt{K_{QR}}$ | C × 1000 |
|---|---|---|---|---|---|---|
| Male, 74 y/old | Yes | 336 | 1 | 0.365 | 0.335 | 1090 |
| Female, 58 y/old | No | 60 | 3 | 0.48 | 0.598 | 802 |
| Female, 52 y/old With taking β-blockers | Yes | 184 | 0 | 0.39 | 0.607 | 642 |
| Female, 52 y/old Without taking β-blockers | Yes | 0 | 0 | 0.425 | 0.72 | 590 |
| Female, 57 y/old | No | 0 | 0 | 0.333 | 0.885 | 376 |
| Male, 58 y/old | No | 0 | 0 | 0.286 | 0.865 | 330 |
| Male, 50 y/old | No | 0 | 0 | 0.281 | 0.9 | 312 |
| Male, 48 y/old | No | 0 | 0 | 0.25 | 0.833 | 300 |

Data shown in the Table demonstrate the monotonic dependence of the aggregated stability measure C (arrhythmia index) on the severity of disturbances of cardiac rhythm. Indeed, the index, C, increases with the increase of the number of PVC and non-sustain VT episodes.

The foregoing is illustrative of the present invention, and is not to be construed as limiting thereof. The invention is defined by the following claims, with equivalents of the claims to be included therein.

That which is claimed is:

1. A method of screening for risk of cardiac arrhythmia in a subject, the method comprising the steps of:
    (a) collecting at least one QT interval data set and at least one RR interval data set from the subject during (i) a stage of gradually increasing heart rate, (ii) a stage of gradually decreasing heart rate, or (iii) both a stage of gradually increasing heart rate and gradually decreasing heart rate;
    (b) separating fluctuations from slow trends in said at least one QT interval data set and in said at least one RR interval data set to provide QT fluctuations and RR fluctuations;
    (c) comparing said QT fluctuations and said RR fluctuations to one another to determine the difference therebetween; and
    (d) generating from the comparison of step (c) a measure of risk of cardiac arrhythmia in said subject, wherein a greater difference between QT fluctuations and RR fluctuations indicates greater risk of cardiac arrhythmia in said subject.

2. The method according to claim 1, wherein said QT and RR interval data sets are collected under quasi-stationary conditions.

3. The method according to claim 1, wherein said stage of gradually increasing heart rate and said stage of gradually decreasing heart rate are each at least 3 minutes in duration.

4. The method according to claim 1, wherein said stage of gradually increasing heart rate and said stage of gradually decreasing heart rate are together carried out for a total time of from 6 minutes to 40 minutes.

5. The method according to claim 1, wherein:
    both said stage of gradually increasing heart rate and said stage of gradually decreasing heart rate are carried out between a peak rate and a minimum rate; and said peak rates of both said stage of gradually increasing heart rate and said stage of gradually decreasing heart rate are the same.

6. The method according to claim 1, wherein said stage of gradually decreasing heart rate is carried out at at least three different heart-rate stimulation levels.

7. The method according to claim 6, wherein said stage of gradually increasing heart rate is carried out at at least three different heart-rate stimulation levels.

8. The method according to claim 1, wherein said stage of gradually increasing heart rate and said stage of gradually decreasing heart rate are carried out sequentially in time.

9. The method according to claim 1, wherein said stage of gradually increasing heart rate and said stage of gradually decreasing heart rate are carried out separately in time.

10. The method according to claim 1, wherein said heart rate during said stage of gradually increasing heart rate does not exceed more than 120 beats per minute.

11. The method according to claim 1, wherein said heart rate during said stage of gradually increasing heart rate exceeds 120 beats per minute.

12. The method according to claim 1, further comprising the step of:
 (e) comparing said measure of risk of cardiac arrhythmia risk to at least one reference value; and then
 (f) generating from said comparison of step (e) a quantitative indicium of risk of cardiac arrhythmia for said subject.

13. The method according to claim 12, further comprising the steps of:
 (g) treating said subject with a cardiovascular therapy; and then
 (h) repeating steps (a) through (f) to assess the efficacy of said cardiovascular therapy, in which a decrease in the quantitative indicium from before said therapy to after said therapy indicates an improvement in cardiac health in said subject from said cardiovascular therapy.

14. The method according to claim 13, wherein said cardiovascular therapy is selected from the group consisting of aerobic exercise, muscle strength building, change in diet, nutritional supplement, weight loss, stress reduction, smoking cessation, p harmaceutical treatment, surgical treatment, and combinations thereof.

15. The method according to claim 13, further comprising the step of assessing from said quantitative indicum the likelihood that said subject is at risk to experience a future cardiac arrhythmia.

16. The method according to claim 1, wherein said data sets are collected by:
 collecting a first QT and RR interval data set from said subject during a stage of gradually increasing heart rate; and
 collecting a second QT and RR interval data set from said subject during a stage of gradually decreasing heart rate;
said method further comprising the steps of:
 (e) comparing said first QT and RR interval data set to said second QT and RR-interval data set to determine the difference between said data sets; and
 (f) generating from said comparison of step (e) a measure of risk of cardiac arrhythmia in said subject, wherein a greater difference between said first and second data sets indicates greater risk of cardiac arrhythmia in said subject.

17. A method of assessing risk of cardiac arrhythmia in a subject, said method comprising the steps, performed on a computer system, of:
 (a) providing at least one QT interval data set and at least one RR interval data set collected from said subject during (i) a stage of gradually increasing heart rate, (ii) a stage of gradually decreasing heart rate, or (iii) both a stage of gradually increasing heart rate and gradually decreasing heart rate;
 (b) separating fluctuations from slow trends in said at least one QT interval data set and in said at least one RR interval data set to provide QT fluctuations and RR fluctuations;
 (c) comparing said QT fluctuations and said RR fluctuations to one another to determine the difference therebetween; and
 (d) generating from the comparison of step (c) a measure of risk of cardiac arrhythmia in said subject, wherein a greater difference between QT fluctuations and RR fluctuations indicates greater risk of cardiac arrhythmia in said subject.

* * * * *